US011036831B1

(12) United States Patent
Mok

(10) Patent No.: US 11,036,831 B1
(45) Date of Patent: Jun. 15, 2021

(54) SYSTEMS, METHODS, AND APPARATUSES FOR COMBINING MEDICATION ADHERENCE AND DIAGNOSTIC LAB SCORES TO DETERMINE INTERVENTION

(71) Applicant: Megan Wai-Han Mok, Pacifica, CA (US)

(72) Inventor: Megan Wai-Han Mok, Pacifica, CA (US)

(73) Assignee: PEOPLECHART CORPORATION, San Francisco, CA (US)

( * ) Notice: Subject to any disclaimer, the term of this patent is extended or adjusted under 35 U.S.C. 154(b) by 350 days.

(21) Appl. No.: 14/986,165

(22) Filed: Dec. 31, 2015

Related U.S. Application Data

(60) Provisional application No. 62/098,867, filed on Dec. 31, 2014.

(51) Int. Cl.
  *G16H 20/00* (2018.01)
  *G06F 19/00* (2018.01)

(52) U.S. Cl.
  CPC .............................. *G06F 19/3456* (2013.01)

(58) Field of Classification Search
  CPC ........ G06Q 50/22; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00;
  (Continued)

(56) References Cited

U.S. PATENT DOCUMENTS 6,578,003 B1 * 6/2003 Camarda ................ B82Y 10/00
                                                        705/3
8,799,204 B1 * 8/2014 Nease, Jr. ........... G06F 19/3481
                                                        706/50

(Continued)

OTHER PUBLICATIONS

New England Healthcare Institute (NEHI). "Thinking Outside the Pillbox: A System-Wide Approach to Improving Patient Medication Adherence for Chronic Disease." Aug. 2009.

(Continued)

*Primary Examiner* — Hiep V Nguyen
(74) *Attorney, Agent, or Firm* — Dorsey & Whitney LLP

(57) ABSTRACT

Systems, methods, and apparatuses for managing patient adherence to prescription medication are disclosed. An adherence manager may receive lab values and prescription fill information from laboratories and pharmacies, respectively. The adherence manager may calculate an adherence score and a lab value score based on the received information. The scores may be combined into a single score. The adherence manager may determine if an intervention with the patient is desirable based at least in part on the adherence score, lab value score, or combined score. The adherence manager may flag the patient, send an alert to a clinician, or send an alert to the patient. The adherence manager may solicit information from the patient and transmit the information to the clinician. The type of intervention initiated by the adherence manager may be based at least in part on the adherence score, lab value score, or combined score.

26 Claims, 17 Drawing Sheets

(58) Field of Classification Search
CPC ........ G16H 70/00; G16H 70/20; G16H 70/40;
G16H 70/60; G16H 80/00
See application file for complete search history.

(56) References Cited

U.S. PATENT DOCUMENTS

| | | | | |
|---|---|---|---|---|
| 9,852,266 | B2* | 12/2017 | Damani | G06F 19/3418 |
| 2006/0031101 | A1* | 2/2006 | Ross | G06F 19/3418 |
| | | | | 705/3 |
| 2009/0281835 | A1* | 11/2009 | Patwardhan | G06F 19/3456 |
| | | | | 705/3 |
| 2013/0096953 | A1* | 4/2013 | Beverly | G06F 19/3418 |
| | | | | 705/3 |
| 2014/0074510 | A1* | 3/2014 | McClung | G06F 19/3431 |
| | | | | 705/3 |
| 2014/0257852 | A1* | 9/2014 | Walker | G06F 19/3456 |
| | | | | 705/3 |

OTHER PUBLICATIONS

US Centers for Disease Control and Prevention. "Chronic Disease Overview." Nov. 14, 2008.
Brown, M.T. et al., "Medication Adherence: WHO Cares?" Apr. 2011.
Fischer, M.A. et al., "Primary Medication Non-Adherence: Analysis of 195,930 Electronic Prescriptions." Feb. 2010.
Ho, P. M. et al., "Medication adherence." 2009.
Osterberg, L. et al., "Adherence to medication." 2005.
Smith, D. L., "Compliance packaging; a patient education tool," American Pharmacy, vol. NS29, No. 2. Feb. 1989.
Willson, M. et al., "Improving Medication Adherence through Collaboration between Colleges of Pharmacy and Community Pharmacies." Jul. 2013.

* cited by examiner

STRATIFICATION OF PATIENTS BY COMPLIANCE THRESHOLDS

COMPLIANCE SINCE: ○ 1 MO  ○ 3 MOS  ○ 6 MOS  ○ 9 MOS  ○ 12 MOS  ● ALL HISTORY  ○ CUSTOM [____] TO [____]

CHRONIC: [DRUG CLASS ▼]  BETA BLOCKERS, CARDIOSELECTIVE, HMG-CoA REDUCTASE INHIBITORS

MED THRESHOLD: [80% ▼]  ☑ BELOW

- ☑ BETA BLOCKERS, CARDIOSELECTIVE
- ☐ BIGUANIDES
- ☐ BRONCHODILATOR COMBINATIONS
- ☐ CARBONIC ANHYDRASE INHIBITOR ANTICONVULSANTS
- ☐ CHOLESTEROL ABSORPTION INHIBITORS
- ☐ COUMARINS AND INDANEDIONES
- ☐ DIPEPTIDYL PEPTIDASE 4 INHIBITORS
- ☐ DOPAMINERGIC ANTIPARKINSONISM AGENTS
- ☐ ESTROGENS
- ☐ FATTY ACID DERIVATIVE ANTICONVULSANTS
- ☐ GAMMA-AMINOBUTYRIC ACID ANALOGS
- ☐ GI STIMULANTS
- ☐ GLUCOCORTICOIDS
- ☐ H2 ANTAGONISTS
- ☑ HMG-CoA REDUCTASE INHIBITORS

INCLUDE: ☐ PATIENTS WITH NO (OR SINGLE) RECOR...

REPORTING OF MATCHED RESULTS
DRUG CLASS: BETA BLOCKERS, CARDIOSELECTIVE

SHOW [25] ENTRIES

[SEARCH PATIENTS]

PRINT REPORT: [SELECT... ▼]

SEARCH: [____]

◆ PATIENT NAME ... HISTORY  ◆ OTHER CLASS(ES) (LAST FILL DATE)

+ EVERETT, BARBARA
  FEMALE 73 YEARS OLD (7/12/1942)  ...2015)  63%  BRONCHODILATOR COMBINATIONS (3/10/2015)
  COUMARINS AND INDANEDIONES (3/10/2015)
  URINARY ANTISPASMODICS (2/20/2015)
  POTASSIUM-SPARING DIURETICS (1/19/2015)
  CARBONIC ANHYDRASE INHIBITOR ANTICONVULSANTS
  (1/19/2015)
  INSULIN (10/4/2015)

| CONDITION "A" | MEDICATION(S) PRESCRIBED FOR CONDITION "A" | |
|---|---|---|
| | GOOD ADHERENCE (COMPLIANCE LEVEL > = "X"% THRESHOLD LEVEL) | POOR ADHERENCE (COMPLIANCE LEVEL > = "X"% THRESHOLD LEVEL) |
| GOOD LAB VALUES (VALUES WITHIN NORMALIZED 0 TO 1 REFERENCE RANGE) | GOOD LAB VALUES / GOOD ADHERENCE (LOW RISK PATIENT)<br><br>HYPOTHESES: LITTLE NEED FOR CLOSE OR COSTLY MONITORING. DO PERIODIC STATUS CHECK. CONSIDER REDUCING DOSE ON MEDICATION. | GOOD LAB VALUES / POOR ADHERENCE (LOW TO MODERATE RISK PATIENT)<br><br>HYPOTHESES: PATIENT HAS MADE IMPROVEMENTS ON LIFESTYLE AND/OR DIET. IF GOOD OUTCOME IS NOT DRIVEN BY PATIENT, CONSIDER POSSIBILITY OF MISDIAGNOSIS OR EFFECTS FROM OTHER CONDITIONS (CO-MORBIDITIES) |
| POOR LAB VALUES (VALUES OUTSIDE OF NORMALIZED 0 TO 1 REFERENCE RANGES) | POOR LAB VALUES / GOOD ADHERENCE (MODERATE TO HIGH RISK PATIENT)<br><br>HYPOTHESES: POOR OUTCOME MAY BE DUE TO INEFFECTIVE TREATMENT, INSUFFICIENT DOSE, ADVERSE INTERACTIONS FROM ANOTHER DRUG, OR MISDIAGNOSIS. | POOR LAB VALUES / POOR ADHERENCE (HIGH RISK PATIENTS)<br><br>HYPOTHESES: PATIENT HAS MULTIPLE REASONS FOR POOR ADHERENCE. FIND OUT REASONS BEFORE CHANGING MEDICATION PREMATURELY. |
| LAB VALUES REFLECTING STATUS ON CONDITION "A". | | |

SYSTEMS, METHODS, AND APPARATUSES FOR COMBINING MEDICATION ADHERENCE AND DIAGNOSTIC LAB SCORES TO DETERMINE INTERVENTION

CROSS-REFERENCE TO RELATED APPLICATION

This application claims the benefit under 35 U.S.C. § 119(e) of the earlier filing date of provisional application No. 62/098,867, filed Dec. 31, 2014.

The entire disclosure of the priority provisional application is considered to be part of the disclosure of the instant application and is hereby incorporated by reference in its entirety for any purpose.

BACKGROUND

About half of all adults in the US, about 120 million people, are diagnosed with at least one chronic condition. The number of chronic health concerns tends to rise with age and by the time adults reach 65 and older, at least 88% of this population has one or more chronic conditions. It is estimated that approximately half of Americans whose conditions are being treated with prescriptions do not take their medications as instructed. It is further estimated that between 20-30% of prescriptions are never filled, and of those filled, about 50% are abandoned after the initial fill. Patient's non-adherence to prescribed therapy may account for 30-50% of treatment failures, and may cost up to $300 billion in avoidable medical expenditures a year.

As a result of the Accountable Care Act and recent changes in payer reimbursements, health care providers are being graded, and either rewarded for meeting quality measures or penalized for failing to meet quality measures and/or for failing to achieve cost reductions related to bringing down preventable admissions to the Emergency Room and bringing down readmissions for the same condition to an acceptable level. It may be possible to reduce the cost of non-adherence and improve patient's health status through active interventions, typically initiated by the clinicians or medical staff in a primary care or hospital setting. However, human intervention is costly and medical staff have limited time and resources for such efforts. Care management typically absorbs 25% of a healthcare provider's budget and may be one of the highest expense items in the operating financials. Existing systems for care follow-up usually require staff to make a phone call to the patient or make an in-person visit to the patient's home. It is not feasible to apply intervention for all patients. In addition, Clinicians don't yet have an electronic or systematic way of identifying patients in poor adherence or to optimally prioritize them so that the patients most in need are optimally matched with available resources.

The reasons for non-adherence are complex. Some factors are attributed to the background of the patient, e.g., poor health literacy, low motivation for self-management, and affordability (cost of prescription). Some factors, to the decisions of the physician, e.g., prescribing drugs with bad side effects, difficult-to-follow instructions, and/or adverse effects due to the presence of other conditions or other drugs, and communication issues. Other factors are attributed to the restrictions imposed by the health system or health care industry, e.g., limited access to quality care, high costs of drugs, care of the same patient performed by multiple physicians, and lack of care coordination and interoperable health information systems. Medical staff or clinicians need better ways to monitor adherence while making decisions about prescriptive treatments for chronic conditions. Far too often, clinicians are tempted to make changes in prescribed therapies before they know whether outcomes may have been hindered by poor patient adherence. In addition, as health care continues to be fluid and multi-faceted, clinicians are in need of more complete and timely access to patient information, especially about medications prescribed by other providers.

BRIEF DESCRIPTION OF THE DRAWINGS

FIG. 11 is an example of a graphical presentation of adherence scores for medical conditions according to an embodiment of the disclosure.

FIG. 14 is an example of a graphical presentation of adherence scores for a list of individual patients according to an embodiment of the disclosure.

FIGS. 15a-c are examples of a graphical user interface for selecting a sub-population from a population of patients according to an embodiment of the disclosure.

FIG. 16 is an example of categorization criteria and hypotheses of patients based on adherence scores and lab values according to an embodiment of the disclosure.

DETAILED DESCRIPTION

Figure 1:
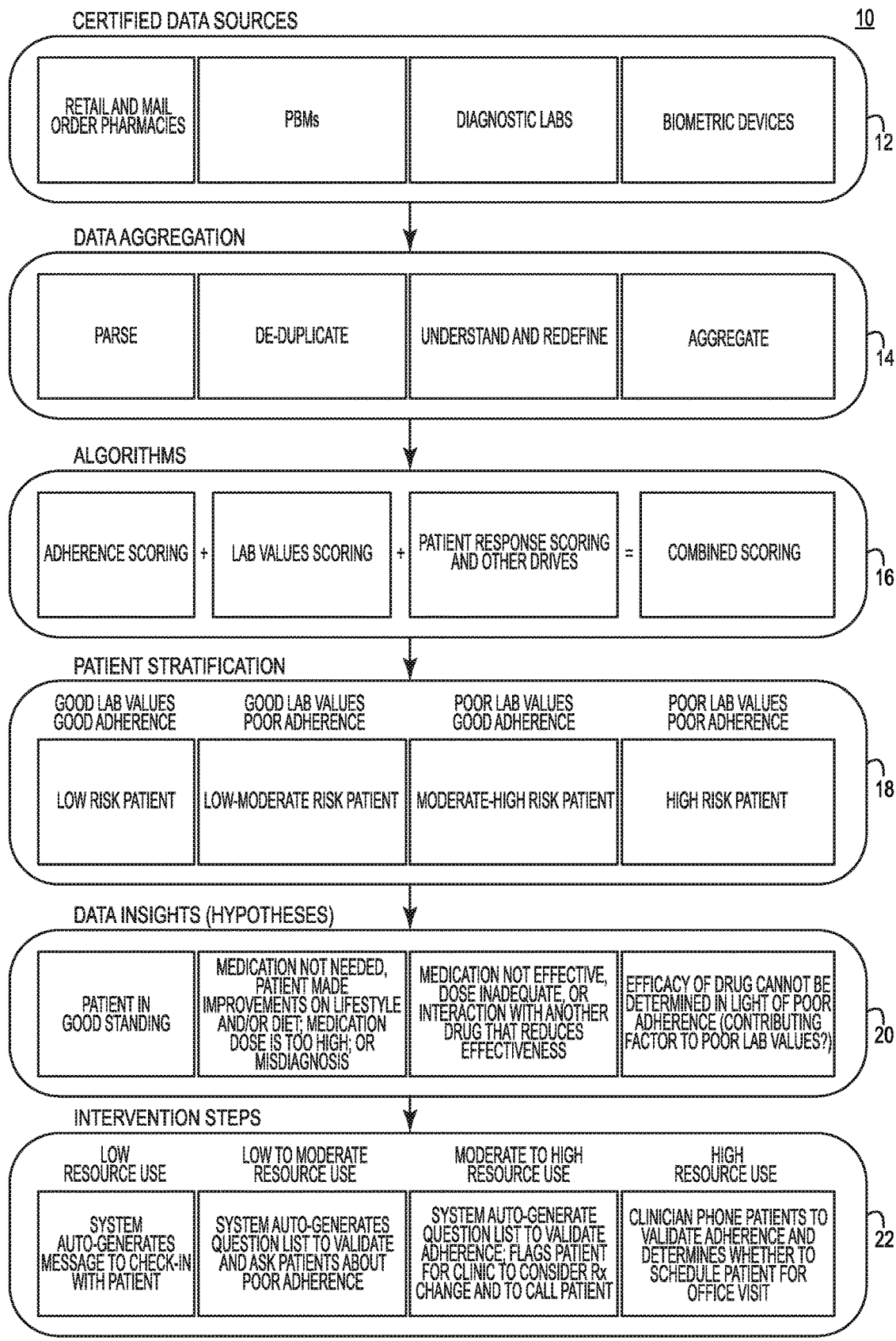
FIG. 1 is a block diagram of workflows according to an embodiment of the disclosure.

Although the following detailed description contains specific details for the purpose of providing a thorough understanding of the subject matter, one of ordinary skill in the art will appreciate that many variations and alterations to the following details are within the scope of the disclosure.

Accordingly, the invention should not be limited to the embodiments and examples described below.

Some portions of the detailed description that follows are presented in terms of algorithms, programs, and/or symbolic representations of operations on data or data bits within a computer memory and/or computer system for example. These algorithmic descriptions and/or representations may employ techniques used in the data processing arts to convey the arrangement of a computer system and/or other information handling system of operation according to such programs, algorithms, and/or symbolic representations of operations.

Example systems and methods described herein may facilitate improvements in the delivery of health care and overall health outcome of patients by analyzing medication adherence (e.g., based on prescription fill data) and diagnostics or biometrics outcomes (based on lab results data) to identify patients where action may be helpful, and to flag those patients for action, and/or to take action on those patients.

Example systems and methods described herein may develop a numerical score related to medication adherence for each patient of a population of patients. The example systems and methods may also develop a numerical score related to health status or outcome for each patient of a population of patients as represented by diagnostic (lab) or biometric values. The scores may be particular to a certain condition—e.g. the scores relate to medication adherence for drugs relevant to the condition and lab or biometric results also relevant to the condition. The scores may be particular to a certain duration of time as the condition progresses over time. The scores for medication adherence and lab or biometric results may be combined to yield a single score in some examples for each patient in the population. These single scores may be used to prioritize the patient population based on their combined rating in medication adherence and health outcome as reflected in the lab or biometric values. These single scores may be used to flag particular patients and/or groups of patients for action. In some examples, a single numerical score per patient may not be used, but an analysis utilizing both the medication adherence and health outcome data may be used.

In this manner, examples of systems and methods described herein may analyze large patient populations to identify sub-populations for which a particular action (e.g. change of medication, change of dose, encouragement to take medication, etc.) would be most appropriate. This identification process may allow for targeted follow-up and, in some cases, may reduce the need for a patient to schedule further time with a physician. Moreover, the combined analysis of medication adherence and condition-based outcome may save physicians time in reviewing patient records to determine a next step—the combined analysis of these factors may be completed in support of, and prior to, any review performed by the physician.

In other examples, examples utilizing the methods and systems described herein may instead facilitate improved delivery of health care and health outcomes of patients by analyzing patient adherence with other treatment regimens (e.g., physical therapy, diets, exercise) along with diagnostic lab data to identify patients where action may be helpful, and to flag those patients for action, and/or take action on those patients.

Historically, the medical industry and its technology suppliers have designed, developed and maintained systems that executed lab orders and reported lab results independently from the systems that have routinely routed and dispensed prescription orders and fills. This separation of systems is consistent with the fact that, within the medical industry, pharmacy/prescription management functions and diagnostic lab functions are performed by different sets of health service providers. The separation allows each system to focus more effectively on specific objectives. At the same time, the culture of independence between pharmacies and diagnostic centers has also resulted in the lack of interoperability between the systems and the lack of common use for the data created by these respective systems.

This separation of prescription and diagnostic systems and lack of interoperability is widespread in the healthcare industry and has kept the industry from creating innovations that would systematically make use of the combined data sets that can be sourced from each of the prescription and diagnostic management systems. In situations where data is stored in separate systems and captured in disparate formats, physicians have had to evaluate their decisions for prescribing certain medications and the results of lab tests without concurrent and organized access to information from these two separate types of systems. For systems that can capture data sourced from each of these independent systems, such as the integration functions of robust electronic medical record (EMR) systems, the display of the medication and lab data sets is usually rendered in entirely separate views or webpages. There are a few sophisticated analytical systems that display prescribed medications and lab values by condition within the same period of time, but none tracks and measures adherence as reflected by the prescription fill data for a specific condition and the outcome of the same condition as reflected by the lab values within the same period of time.

Embodiments of the disclosure may provide a new type of reporting of patient's health status, one that sources data from both of these types of historically-independent source systems and one that may create a set of decision metrics around the data that would explain the causes for good or poor health outcomes based on examination of patient's fill behavior (e.g., adherence to prescription instructions) and physician's decision to prescribe specific medication for treatment (e.g., adherence to evidence-based guidelines of care). The data workflows may include a series of intricate steps to clean, normalize, arrange, and aggregate data in ways that may help narrow the set of likely cause(s) for poor outcomes of a specific condition so that healthcare providers can take the appropriate steps for intervention.

FIG. 1 is a block diagram of an example workflow 10 according to an embodiment of the disclosure. At block 12, data may be generated and/or received from one or more service provider sources (e.g., pharmacies, diagnostic labs nation-wide) for one or more patients. The raw data from the one or more sources may be aggregated and/or formatted at block 14. The processed data may then be used to calculate one or more scores at block 16. Score calculation is described in more detail below. The calculated scores may be used to categorize patients into one or more groups at block 18. The patients may be prioritized across and/or within groups. One or more hypotheses may be generated at block 20 based, at least in part, on the categorization of the patient. Based at least in part on the hypotheses, one or more interventions is recommended and/or carried out at block 22.

Embodiments of the disclosure may be driven by the fundamental philosophy that condition-based outcome (e.g., as reflect in the lab values) may be impacted by the patient's behavior (e.g., adherence to treatment) and by the physician's decision/choice of medication prescription (e.g., adherence to best-practice). The responsibility of adherence to best-practice or to industry-standards for success in treatment is a shared responsibility for both participating roles (e.g. patient and physician). Enabling healthcare decisions to be made based on lab values that are placed in context of patient's adherence offers providers a new and more systematic way to accurately identify the likely cause (s) for poor outcomes.

Major studies have found that lab values are the basis for approximately 70% of all new healthcare decisions. When healthcare providers observe poor lab values after prescribing best-practice medications to address a patient's issues, they frequently conclude that the previous prescription was not sufficiently effective to produce the desired results, and then proceed to prescribe an alternative medication. Unfortunately, poor lab values are just as frequently attributed to the patient's failure to stay with a prescribed treatment as they are the result of ineffective treatment.

Embodiments of the disclosure may combine medication adherence data with lab values to produce a combined set of clean, aggregated and normalized set of data, upon which classification metrics and scoring algorithms may be applied to identify and prioritize patients from high to low risk based on their adherence scores, lab scores, or combined adherence and lab scores. The segmentation of patients into various risk categories may help reduce the case load of care management personnel by directing them to focus on the patients most in need of human-assisted intervention. The combination of adherence and lab data, when normalized and scored, may produce a set of metrics that may be used to drive the segmentation of patients into the categories reflective of their risk levels and the limited set of likely hypotheses that may explain the causes for poor outcome. The validation of these hypotheses may determine the subsequent use of automated versus human-assisted form of intervention. An illustrative example of patient segmentation includes:

High risk: Poor lab values/poor adherence
Medium-to-high risk: Poor lab values/good adherence
Medium risk: Good lab values/poor adherence
Low risk: Good lab values/good adherence Although four segments are described above, more or fewer segments may be used. The synthesis of complex issues into a metric may help categorize and reduce the downside risks of clinicians drawing the wrong conclusions. The formation of hypotheses for each category of patients may help clinicians think about the distinction between the behavioral issues that may impede treatment from the symptomatic issues that may require a change in medications. The emphasis on these differences may help clinicians quickly and more accurate identify the reasons for poor health outcomes. For example, patients may be stratified into any of these behavioral/outcome metrics that may help healthcare provider:

(1) Avoid prematurely abandoning best-practice treatment regimen when the patient's poor adherence to the regimen is likely the primary cause for the poor lab values.

(2) Raise the possibility of misdiagnosis or improved lifestyle factors when patient is in poor adherence in filling their medications, yet the lab values are good or improving.

(3) Consider a change in medication (e.g., dose, type) when the patient is in good adherence, yet the lab values are poor or have deteriorated from previous lab values. This particular situation may also raise the question of effects from adverse drug interactions (counter-indications), especially if the patient is taking medications for treating other conditions.

By correlating the patient's fills/refills of specific medications with their lab values for the same condition and over the same time period, embodiments of the disclosure may help clinicians distinguish the situations that call for a change in previous choice of treatment versus steps to help patients improve adherence as the best option for moving forward in the care delivery.

The relationship between adherence (e.g., as reflected by the dates of medication fills) and lab values associated with a condition may help clinicians: increase the proportion of times that prescriptions are consistent with best-practice treatments; focus on improving patient adherence when adherence is likely the primary cause; question the validity of diagnosis and probability of effects from patient's other conditions; and/or raise the possibility of lifestyle or diet improvements that may call for reduction or discontinuation of medication.

Embodiments of the disclosure may establish a spectrum of new health data metrics that place treatment decisions in a context of the information needed by clinicians (e.g., behavioral and clinical data) that may systematically produce better healthcare outcomes. It may also help providers narrow a decision set on appropriate intervention (e.g., change treatment choices or improve patient's adherence).

For example, is the patient adherent in filling prescribed medication for treatment of a condition whose outcome is reflected by specific lab result or set of lab values?

If "No:" What can be done to improve patient adherence to the level required to achieve desired effect of best-practice treatment regimen? What other medications or treatment regimens should be considered that may help the patient improve adherence, for example, reduce bad side effects, while keeping in mind the need for treatment of the patient's primary condition?

If "Yes:" Is the prescribed regimen appropriate for this patient in its desired impact on health outcomes (e.g., as reflected in the patient's lab values)? Should changes be considered in the prescribed treatment (e.g., changing the dose or medication type)?

Using this reporting and stratification metric, an embodiment of the disclosure may include a type of lab reporting and measurement system. The system may enable physicians to be systematically aware of the longitudinal patterns of patient's fill behaviors of a prescription or a group of prescriptions used for treatment of a specific condition while reviewing lab values of the same condition as part of the process for making new healthcare decisions. The combination of diagnostic or biometric data and medication fill data may help narrow the universe of possible reasons behind poor health outcomes to a manageable and narrower list of likely explanations (e.g., hypotheses) derived from behavioral drivers (e.g., adherence) and clinical drivers (e.g., appropriateness of treatment).

As explained further below, the hypotheses drawn from these metrics may include a message prompt for reviewing need to change treatment choices or need to engage the patient in order to improve adherence. In a very simple example of metrics, patients may be placed into one of four quadrants based on their individual "good" or "poor" lab values and "good" or "poor" adherence. The quadrant approach promotes greater understanding of the possible factors that can influence the progression of patient's condition and reduce the risk of changing treatment regimen prematurely or not soon enough.

Compared to the current decision-making process based solely on the review of lab values, embodiments of the disclosure may help physicians first determine whether the issue of patient adherence might explain the poor outcomes reflected in the lab values. The advantage of linking adherence and lab values to the same condition may be useful in situations when patients are being treated for multiple conditions (co-morbidities) and prescribed multiple medications, hence making it difficult to gauge the impact of specific medications on the outcome of specific conditions. Embodiments of the disclosure may provide physicians a systematic and focused approach that may limit the scope of information to that which is relevant for decision-making, condition by condition.

The systematic approach of combining lab values with relevant medication adherence data may also allow providers and patients with ability to determine whether the results show gaps or are aligned with expected results specified by the national guidelines for evidence-based care. The results revealed by combining lab values with medication adherence may bring clinical and behavioral factors closer in alignment, towards best practices for improving condition-based outcomes.

Minimal threshold levels or criteria may be used to allocate patients to different groups (e.g., quadrants) and thresholds may be set at different levels for different segments based on their population profile or predispositions. Threshold levels may be calculated or predetermined. Criteria may include, but is not limited to, patient's condition (s), patient's demographics (population profile being treated), guidelines for treatment that are specific to an individual healthcare provider, and level of overall resources and time available to follow-up on patients with various conditions, characteristics, and/or risk levels.

A clinician may treat a patient for an acute or chronic condition (e.g., pneumonia, diabetes, high blood pressure, heart failure, coronary artery disease) and prescribe a medication to the patient to help treat the condition. The clinician may provide a written prescription for the patient to take to a pharmacy and/or submit the prescription electronically to the pharmacy. The clinician may also order laboratory tests and/or biometric data (e.g., weight, blood pressure) to be collected from the patient. The lab values (which may include biometric data) may indicate whether a desired health outcome of the treatment is being achieved. The clinician may use an adherence manager as part of a medication adherence system to help determine whether the patient is adherent to the prescription (e.g., fills the prescription at timely manner or at specified intervals of time) and/or determine whether the patient's lab values indicate the desired outcome for the condition is being achieved. The clinician may use the adherence manager for multiple patients being treated for conditions.

The adherence manager may alert the clinician when the patient is non-adherent to the prescription medication and/or the lab values indicate a suboptimal or less-than-desired outcome. The adherence manager may solicit information from the patient to help determine reasons for non-adherence and/or health outcomes. The adherence manager may provide the information from the patient to the clinician. The adherence manager may flag certain patients for intervention by the medical staff or clinician and/or rank patients based on the patient's adherence, lab values, and/or other information. Intervention may be performed by the adherence manager by sending an automated alert to the patient. Less resource-intensive form of intervention performed on flagged patients may include calling the patient, requesting additional diagnostic tests and/or biometric information, making a change to the prescription medication (e.g. drug, dosage) and/or requesting involvement from other staff. For example, a clinician may contact a social worker to get in touch with the patient if the adherence manager alerts the clinician that the patient indicated non-adherence was due to an inability to afford a prescription medication. Other types of low resource-intensity intervention may be used. The ranking or prioritization of patients based on their combined scores help determine the cost-intensity of resources to use for intervention, which can range from an automated message (e.g., text, e-mail, voicemail), to a short telephone call, to a request for in-person appointment with the doctor.

Figure 2:
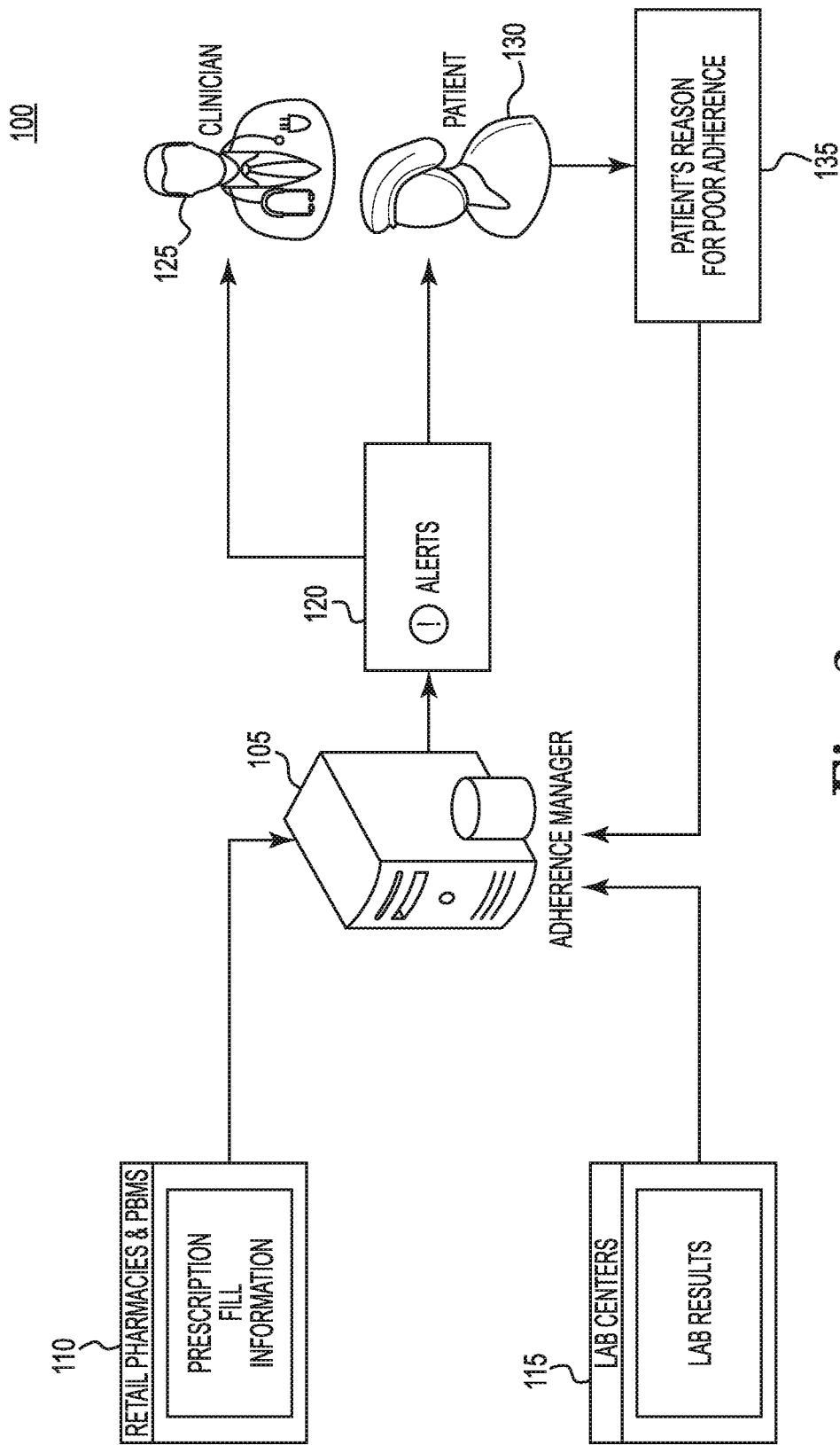
FIG. 2 is a block diagram of an overview of a medication adherence system including an adherence manager according to an embodiment of the disclosure.

FIG. 2 is a block diagram of an overview of a medication adherence system 100 including an adherence manager 105 according to an embodiment of the disclosure. The adherence manager may be implemented using a computing system, such as a server, desktop, laptop, tablet, cell phone, or other computing device which may be programmed to perform some or all of the functions described herein with respect to the adherence manager. To program the computing system to perform functions, the computing system may be provided with or in communication with one or more computer readable media (e.g. a memory) that is encoded with executable instructions, which when executed, cause the computing system to perform some or all of the functions described herein with respect to the adherence manager. The adherence manager 105 may receive prescription fill information 110 from retail pharmacies, prescription-by-mail pharmacies, and/or other authorized prescription fillers. The adherence manager 105 may also receive lab values 115 (e.g., diagnostic results and/or biometric data) from laboratory centers, hospitals, clinics, and/or other facility that may perform and/or analyze laboratory tests. In some examples, the lab values 115 may include biometric data instead of or in addition to diagnostic results. For example, height, weight, age, blood pressure, or any combination of observable data may be provided as lab values 115. In some examples, the lab values 115 may be provided by a biometric sensor (e.g. scale, blood pressure monitor, thermometer, camera) which may be in communication with the adherence manager 105. The adherence manager 105 may analyze the medication data 110 and the lab values 115 for one or more patients. Based on the analysis, the adherence manager 105 may send alerts 120 to a clinician 125 and/or a patient 130. The alerts 120 may prompt the clinician to contact the patient 130. The alert 120 may prompt the patient 130 to provide the adherence manager 105 with additional information. For example, the alert 120 may request reasons why the patient 130 is not compliant with their medication. The patient 130 may provide a response 135 to the adherence manager 105. Based on the response or non-response, the adherence manager 105 may or may not send an alert 120 to the clinician 125.

Figure 3:
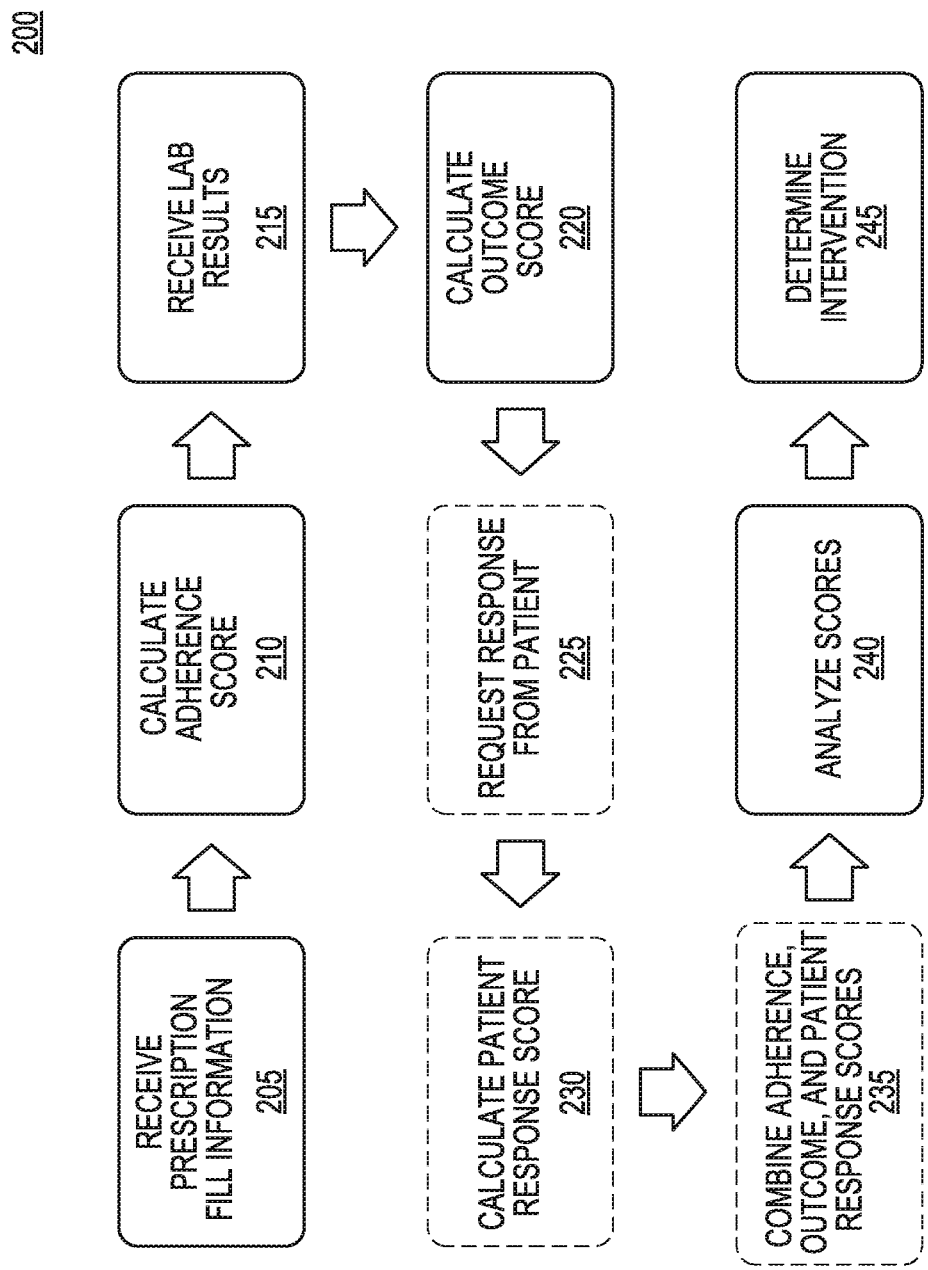
FIG. 3 is a flow chart of a method according to an embodiment of the disclosure.

FIG. 3 is a flow chart of a method 200 according to an embodiment of the disclosure. The method 200 may be performed by an adherence manager, for example adherence manager 105 shown in FIG. 2. The adherence manager may receive prescription fill information at block 205. The prescription fill information may include whether or not the prescription was filled, the day since the last fill, and/or the day of the next scheduled fill. The adherence manager may analyze the prescription fill information to calculate an adherence score at block 210. The adherence score may be a numerical value indicative of the degree of prescription adherence is being achieved by the patient. The adherence manager may receive lab values at block 215. The adherence manager may analyze lab values to calculate a lab value score at block 220. The lab value score may be a numerical value indicative of how well a health outcome for a condition is being achieved. The lab value score may be based on lab values (e.g. diagnostic results and/or biometric data). For example, a lab value score for a patient being treated for high cholesterol may be based, at least in part, on how close the low-density lipoprotein (LDL) levels from the lab values were to a normal range for LDL. In some embodiments, the adherence manager may request a response from a patient (e.g., via text message) at block 225. The adherence manager may then calculate a patient response score based, at least in part, by a response received from the patient at block 230. In some embodiments, the adherence manager may combine the adherence score, the lab value score, and/or patient response score into a single combined score at block 235. In some embodiments, the combined score may be calculated from the lab score and adherence score prior to requesting a response from the patient. The adherence manager may analyze the combined score, adherence score, lab value score, patient response score, or any combination thereof at block 240. The adherence manager may compare the adherence score, lab value score, and/or combined score to threshold values. If one or more scores are below a threshold value, the adherence manager may determine an intervention may be necessary at block 245.

The method 200 is not limited to being performed in the order illustrated in FIG. 3. For example, blocks 205 and 210 may be performed after blocks 215 and 220. Blocks 205 and 215 and/or blocks 210 and 220 may occur simultaneously in some embodiments. Other block arrangements may also be possible.

Figure 4:
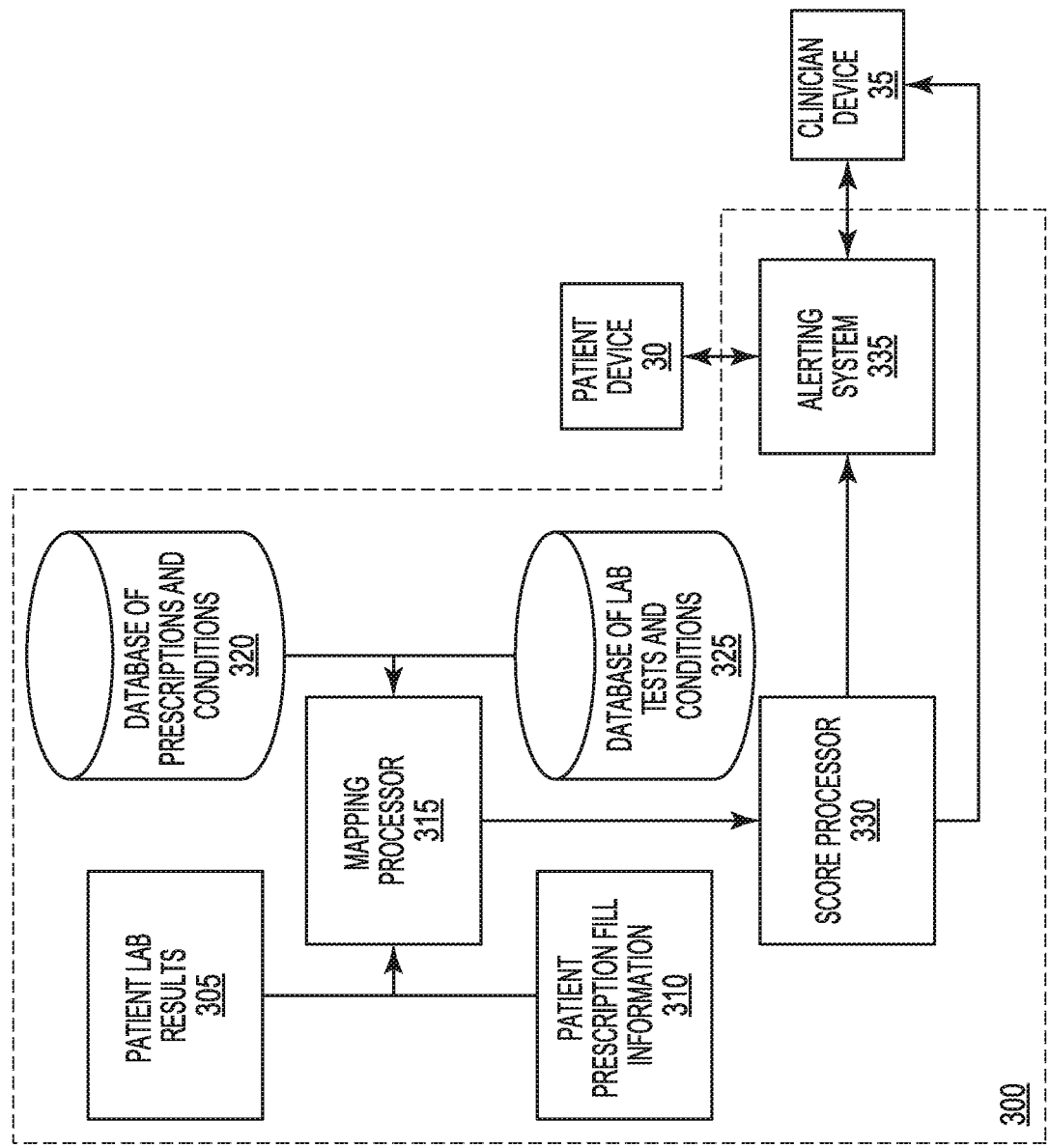
FIG. 4 is a block diagram of an adherence manager according to an embodiment of the disclosure.

FIG. 4 is a block diagram of an adherence manager 300 according to an embodiment of the disclosure. The adherence manager 300 may be used to implement adherence manager 105 shown in FIG. 1 in some examples. The adherence manager 300 may include a first memory 305 storing patient lab values in electronic form. A second memory 310 may be included and store patient prescription fill information in electronic form. In some embodiments, the first and second memories 305, 310 area single memory storing both patient lab values and prescription fill information. The patient lab values and prescription fill information stored in the memories 305, 310 may have been received from a remote computer system (not shown) accessible to the adherence manager, uploaded from a computer readable medium (e.g., USB drive, CD ROM) to the adherence manager 300 through an I/O device (not shown), and/or manually input by a user through a user input device (not shown).

The adherence manager 300 may include a first database 320 that may store an association of prescription medications and which condition or conditions each prescription medication may be relevant to. A second database 325 may include a database of diagnostic tests and/or biometric information and which condition or conditions the diagnostic tests and/or biometric information are used to monitor.

The memories 305, 310 and databases 320, 325 may be accessible to one or more processors included in the adherence manager 300. For example, a mapping processor 315 may be included in the adherence manager 300. The mapping processor 315 may be configured to receive lab values and prescription fill information for a patient from the memories 305, 310. The mapping processor 315 may access the databases 320, 325 to determine which lab values and which prescriptions correspond to which conditions. The mapping processor 315 may then determine which lab values and prescription fill information for the patient correspond to the same condition. For example, a patient taking a statin drug for high cholesterol may have prescription fill information in memory 310. The patient may have a variety of lab values including blood test results, hearing test results, and vision test results in memory 305. The hearing and vision test results may have no relation to the desired health outcome for which the statin drug has been prescribed. The mapping processor 315 may discard the hearing and vision test results based on corresponding conditions for those tests found in the database 325. In this manner, adherence to a particular prescription for a specific condition is not obfuscated by unrelated outcomes by the adherence manager 300. In some examples, the mapping processor 315 and the score processor 330 may be implemented using a same processor.

A score processor 330 may receive prescription fill information and lab values corresponding to the same condition or conditions from the mapping processor 315. The score processor 330 may calculate adherence and lab value scores based, at least in part, on the information received from the mapping processor 315. In some embodiments, the mapping processor 315 and the score processor 330 may be implemented as a single processor or processing unit. The score processor 330 may combine the adherence and lab value scores into a combined score in some embodiments.

For the calculation of adherence score, industry standards Proportion of Days Covered (PDC) or Medication Possession Ratio (MPR) may be used to produce the adherence score in some embodiment. In our invention, we have used some modified form of the industry standard that takes into account and carries over an accounting of excess inventory due to early fills (or surplus). The modified standard is calculated across any interval of time (last 30, 90, 180, 360 days or since history of data was captured) as:

$$\text{Adherence \%} = \frac{\text{Expected Days Supply}_{(\text{for any period, or any consecutive series of fill periods})}}{\text{Actual Days Elapsed}_{(\text{between fills or consecutive series of fills})}} \quad \text{Equation (1)}$$

The Days Supply is the number of days of prescribed medication dispensed to the patient for any given fill period, plus the days of surplus (or days of supply left-over as of the beginning of the fill period). Alternatively, cumulative Days Supply is the number of days of prescribed medication dispensed to a patient across multiple fills within the cumulative time period, plus the days of surplus (or days of supply left-over as of the beginning of the cumulative time period). Correspondingly, the Days Elapsed is the actual number of days passed between fills; or (for a cumulative fill period) the number of days between the date of an initial fill and the date of the last fill within the cumulative time period.

If the patient does not fill a prescription at a timely manner as represented by the Expected Days Supply, they may not have enough supply of the medication to take at the desired dosage level during the period between prescription fills. When the adherence ratio (or score) falls below a desired threshold value (e.g. 87%), the adherence manager 300 may determine the patient is non-adherent to the prescription. In some embodiments, the maximum adherence score is 100%, but other scaling methods may be used.

In some embodiments, prescription fill information for multiple medications that are used for treating a condition may be used to calculate multiple adherence scores. The adherence scores may be considered separately and/or averaged into a single adherence score reflecting the patient's total adherence score for the condition. The adherence score for each medication associated with the condition may be weighted equally or given different weights when combined into an average adherence score. Examples of weighted average methods may include, but are not limited to, factoring in a number of days on the medication, the relative risk of the medication (counter-indications or side effects), and the severity of condition each medication is used to treat.

In some embodiments, a lab or biometric lab value score may be normalized by expressing actual lab values relative to the terms that define the reference or normal range of results associated with a given test type. When patients repeat the taking of same tests in different diagnostic centers, there is a need to normalize the lab values in order to be able to compare them across time. Typically, the reference range is defined by high and low values that represent the end points of a normal range, where actual values that fall within the range are considered normal results and values that fall outside are considered abnormal. For some lab tests, reference for normal has only one value, either a maximum (ceiling) or minimum (floor) value. The reference values for normal range are unique to each diagnostic lab centers and based on the calibration method and equipment used (these values are displayed as the normal range in a lab report). Ratios or percentages are used to represent the magnitude between actual value and end values of the reference range. The formula takes the difference between the actual value and the low value of the reference range and divide that by the magnitude between the high and low values of the reference range for the same test type. For example, LDL may have a normal range of 70-130 mg/dL. In this example, 70 mg/dL may be a low reference value and 130 mg/dL may be a high reference value of the normal range. The lab value score (or interchangeably lab score) may be calculated as:

$$\text{Normalized Lab Value} = \frac{(\text{Actual Result Value} - \text{Low Reference Value})}{(\text{High Reference Value} - \text{Low Reference Value})} \quad \text{Equation (2)}$$

Equation (2) reflects normalized values. These values are then averaged and converted to lab scores that represent the amount of deviation from normal with 1 defined as normal and anything less than 1 defined as having values that fall outside of normal. When normalized value has a value between 0 and 1, it is between the low and high end values of the normal reference range. When the lab value score falls below the normalized value of 0 or rises above 1, the adherence manager 300 may determine the patient has abnormal lab values. In some embodiments, the lab value scores may be normalized such that the highest possible score is 100%.

Biometric information may also be used to calculate a lab value score with Equation (2). For example, a patient's blood pressure may be measured at an office visit. The measured blood pressure may be used as the Actual Result Value, and a desired blood pressure range may be used to obtain the High Reference Value and Low Reference Value.

In some embodiments, multiple diagnostic results and/or biometric information relating to a condition may be used to calculate multiple lab value scores. The lab value scores from the multiple lab values (which may be or include biometric information) may be considered separately and/or combined into a single lab value score. The lab value scores may be weighted equally or given different weights when combined into a single lab value score. For example, a clinician may weight a patient's blood pressure more heavily than the patient's change in body weight.

In some embodiments, a combined lab value score may only combine those lab value scores based on lab results for a specific condition. The adherence manager may link specific conditions to a specific drug and/or drugs. The drug and/or drugs may be linked to a lab result and/or results by the adherence manager. This may prevent normal lab results for one condition (e.g., diabetes) from masking abnormal lab results for a separate condition (e.g., high cholesterol). This may prevent lab results unrelated to the effectiveness of a medication from affecting the lab value score of a patient.

In some embodiments, the adherence score and the lab value score may be combined to generate a combined score. In some embodiments, the combined score is a simple average of the two scores. In some embodiments, the combined score may be generated by adding the lab value score to the adherence score when the lab value score is within a normal range (e.g., between 0-100% when normalized), and multiplying the lab value score with the adherence score when the lab value score is outside the normal range (e.g., below 0% or above 100%). This method of calculating a combined score may allow undesirable lab values to weigh more heavily on the adherence manager's 300 determination of whether an intervention is appropriate.

In some embodiments, the combined score is calculated by:

$$\text{Combined score} = \text{Adherence Score} + \text{Outcome Score} - (100\% - \text{Lab Value Score}) \quad \text{Equation (3)}$$

In some embodiments, the combined score is calculated by:

$$\text{Combined score} = \text{Adherence Score} + \text{Lab Value Score} - (\text{Adherence score} * \% \text{ of Lab Value Score Outside Normal Range}) \quad \text{Equation (4)}$$

Equations (3) and (4) may allow a single equation to be used for calculating the combined score, regardless of whether the lab value score falls within a range of normal values. However, the first method of calculating a combined score may reduce the likelihood of overlap between indications of the adherence and/or lab value score.

The methods described for calculating the adherence, outcome, and combined scores are exemplary and should not be construed as limiting the scores to being calculated by the described methods. Other methods of calculating the adherence, outcome, and/or combined scores may be used.

Still referring to FIG. 4, the score processor 330 may send a signal to an alerting system 335, based, at least in part, on one or more of the calculated scores. For example, the score processor 330 may send a signal to the alerting system 335 when one or more of the scores are below a threshold value. The score processor 330 may send one or more of the scores to a clinician device 35. The clinician device 35 may be a desktop computer, a hospital mainframe, a tablet computer, a mobile phone, and/or another computing device. The alert to the clinician device 35 may be sent as an automated message such as a text message, an e-mail, an automated phone call, a push notification, and/or flagging the patient's record in the clinician device 35.

The alerting system 335 may send alerts to a patient device 30 based, at least in part, on one or more of the calculated scores. The patient device may be a desktop computer, a tablet computer, a mobile phone, and/or another computing device. The alert to the patient device 30 may be a text message, an e-mail, an automated phone call, a push notification, and/or other alert.

The alerts sent to the patient device 30 may solicit information from the patient. For example, the alert may request the patient's reason for poor adherence with a prescription medication and/or availability for a doctor's appointment. The alerting system 335 may receive the information from the patient device 30 and provide the information to the clinician device 35. The alerting system 335 may also notify the clinician device 35 when information was solicited from the patient, but no response was received from the patient device 30. In some embodiments, the alerting system 335 may provide a response from the patient the score processor 330 to generate a response score and/or calculate a combined score. For example, the score processor 330 may reduce the combined score if the patient indicates poor adherence is due to negative side effects. Continuing this example, the score processor 330 may increase the combined score if the patient indicates poor adherence is due to making healthy lifestyle changes that reduce the need to take the medication. Other patient responses and modifications to the combined score may be used.

The alerting system 335 may provide a recommended intervention for the patient to the clinician device 35. The alerting system 335 may provide the recommendation based, at least in part, on the adherence score, lab value score, patient response score, and a combined score that represent the aggregation of all of the above, and/or a combination thereof.

Figure 5:
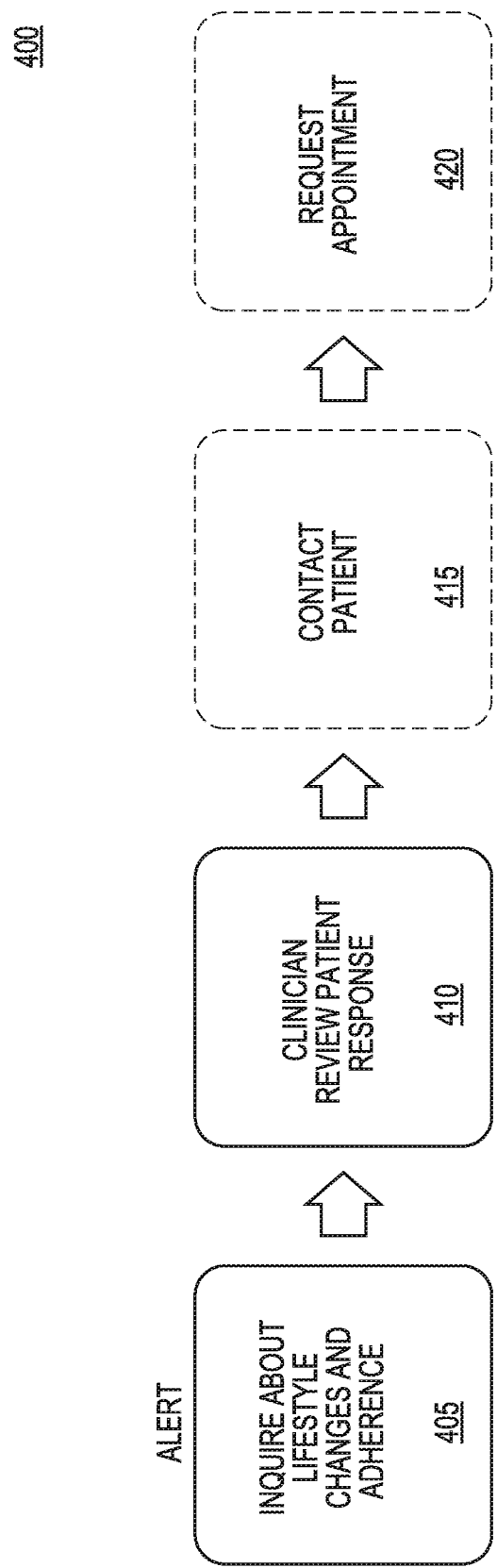
FIG. 5 is a flow chart of a possible intervention initiated by an adherence manager according to an embodiment of the disclosure.

FIG. 5 is a flow chart of possible interventions initiated by an adherence manager, such as adherence manager 300 illustrated in FIG. 4, according to embodiments of the disclosure. If the adherence manager determines that both the adherence score and lab value score are above or exceed threshold values, then no intervention may be recommended, and no alerts may be sent.

FIG. 5 illustrates a possible intervention 400 in response to the adherence manager determining the adherence score is below a threshold value and the lab value score is above a threshold value. That is, the patient is found to be non-adherent to a prescription medication, but the patient's lab values (which may be or include biometric information) indicate that a desired outcome is being achieved. For example, a patient's blood pressure may be in a normal range despite the patient's failure to fill a heart medication prescription. An alerting system may send an alert (e.g., text message) to a patient inquiring about reasons for non-adherence and possible lifestyle changes at block 405. The patient may have made lifestyle changes that make the prescription unnecessary. Continuing the previous example, the patient may have switched to a low sodium diet and started an exercise program, which successfully control the patient's blood pressure without the heart medication. If the patient responds to the alert sent at block 405, the alerting system may send the response to the clinician. The clinician may review the response at block 410, and may determine whether or not further action is required. If so, the clinician may contact the patient at block 415 and/or trigger the alerting system to contact the patient at block 415. If the patient does not respond to the alert sent at block 405, the alerting system may notify the clinician to contact the patient at block 415. The clinician may request the patient come in for an appointment and/or solicit additional information from the patient at block 420. In some embodiments, the alerting system may contact the patient to request an appointment.

In some embodiments, a possible intervention may be in response to the adherence manager determining the adherence score is above a threshold value and the lab value score is below a threshold value. That is, the patient is adherent to their prescription medication, but the patient is failing to exhibit a desired outcome in their lab values (which may be or include biometric data). A clinician may need to adjust the dosage and/or type of medication prescribed to the patient. The alerting system may send an alert to the patient. The alert may request the patient set up an appointment with the clinician and may also inquire about lifestyle changes that may compromise the effect of a medication. If no response is received from the patient, the alerting system may notify the clinician to contact the patient.

In response to the adherence manager determining both the adherence score and the lab value score are below threshold values. The alerting system may send an alert that may request the patient set up an appointment with the clinician and inquire about reasons for non-adherence. If the patient responds, the alerting system may provide the patient's response to the clinician. This may allow the clinician to have appropriate staff and/or alternative treatment plans in place before the appointment. For example, a clinician may arrange to have a social worker present if the patient states reasons for non-adherence include financial struggles. The clinician may arrange to have a meeting with another clinician treating the patient to coordinate care if the patient states reasons for non-adherence include drug interactions and/or unwanted side effects. If no response is received from the patient, the alerting system may notify the clinician to contact the patient.

In response to the adherence manager determining the adherence score is below a threshold value, but no lab value score is available. A lab value score may be unavailable if no lab values have been received by the adherence manager. The clinician may not have ordered diagnostic tests or the patient may have failed to have the diagnostic tests performed. The alerting system may send an alert to the patient that solicits reasons for poor adherence to the prescription medication. If the patient responds, the alerting system may send the response to the clinician. The clinician may review the response to determine if further action is necessary. If so, the clinician may contact the patient or trigger the alerting system to contact the patient. If no response is received from the patient, the alerting system may notify the clinician to contact the patient.

In some embodiments, an adherence manager may include and/or interact with software and hardware components that provide data in graphical form on an electronic display. The adherence manager may include an electronic display and/or provide data for display on another device, for example, the clinician device 35 illustrated in FIG. 4. Data may include adherence score, lab value score, combined score, drug type, dates, patient data, and/or other information.

FIGS. 6-14 illustrate example graphical presentations. The graphical presentations may be provided, for example, on a display of a computing system (e.g. server, desktop, laptop, tablet, cellular phone, robot, appliance, automobile, or medical equipment). The computing system may be programmed with software (e.g. provided with executable instructions causing the computing system to perform) for displaying one or more of the graphical presentations as a portion of a graphical user interface using data provided by the adherence manager, which may or may not be implemented using the computing device providing the graphical presentation.

Figure 6:
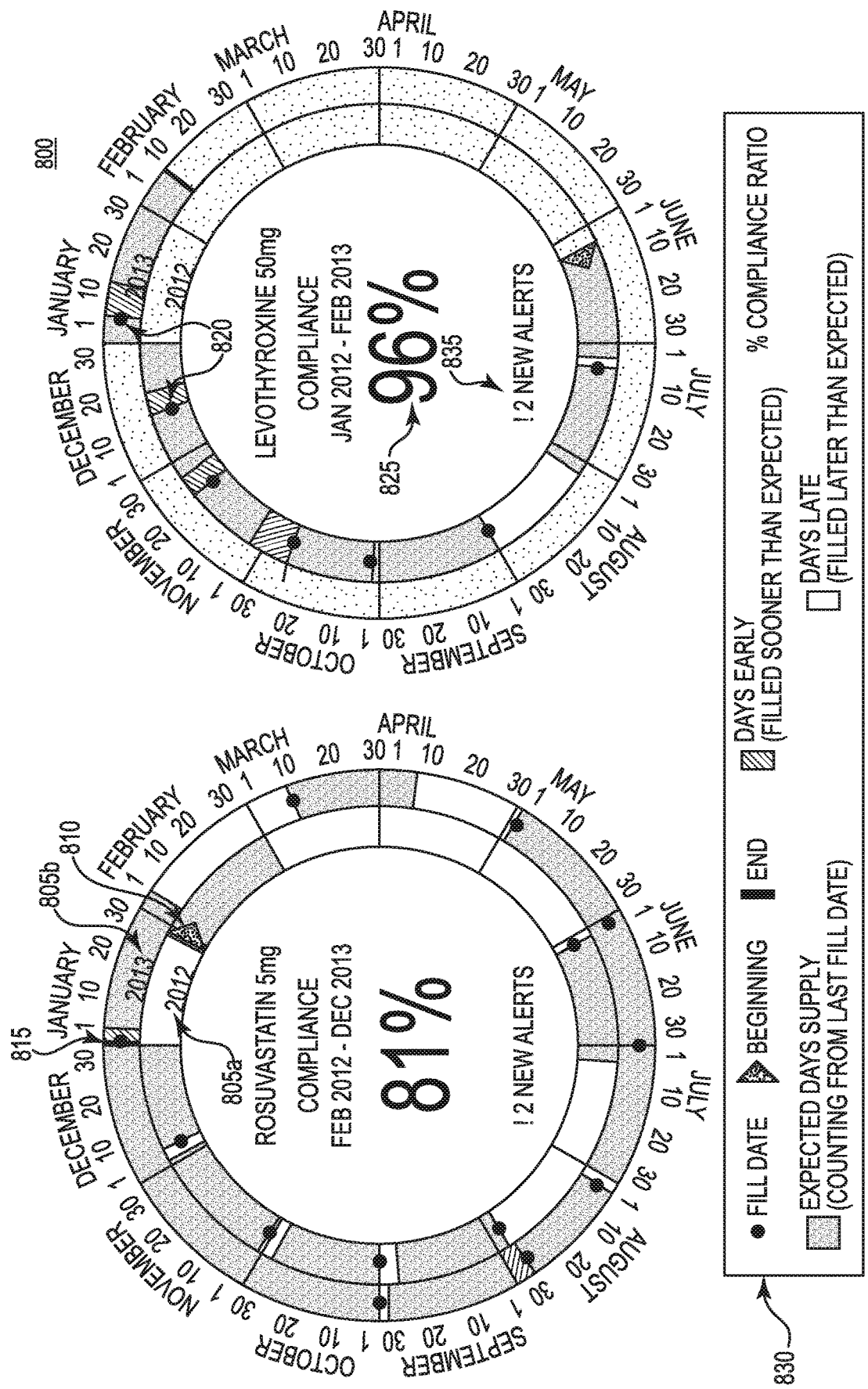
FIG. 6 is an example of a graphical presentation of prescription fill information according to an embodiment of the disclosure.

FIG. 6 is an example of a graphical presentation 800 of prescription fill information according to an embodiment of the disclosure. As shown in the example of FIG. 6, a patient has been prescribed two medications rosuvastatin and levothyroxine. The period of time of each prescription is illustrated by concentric rings 805a, 805b. Each ring 805a-b corresponds to a calendar year, and the months are labeled around the outermost concentric circle 805b. An arrow 810 indicates when the prescription was started by the patient. In the case of rosuvastatin, the patient started the medication in late January 2012. A thick line 815 indicates when the prescription expired and/or was discontinued. In the case of rosuvastatin, the prescription ended on Jan. 1, 2013. Circles 820 may indicate the dates on which the patient filled the prescription. Based on these dates, the adherence manager may calculate the adherence score 825. In some embodiments, the graphical presentation 800 may include different colors and/or shadings of different time periods on the concentric rings 805a-b that may reflect the patient's level of adherence during the time period. The graphical presentation 800 may further include a legend 830 to correspond the different colors and/or shadings to different adherence levels. The graphical presentation 800 may include a visual cue 835 to indicate the patient has been flagged and/or an alert has been sent by the adherence manager to the patient and/or clinician. Although circles, arrows, and lines are used in the example shown in FIG. 8, other symbols may be used. For example, "X" may be used instead of circles 820 to indicate fill dates.

Figure 7:
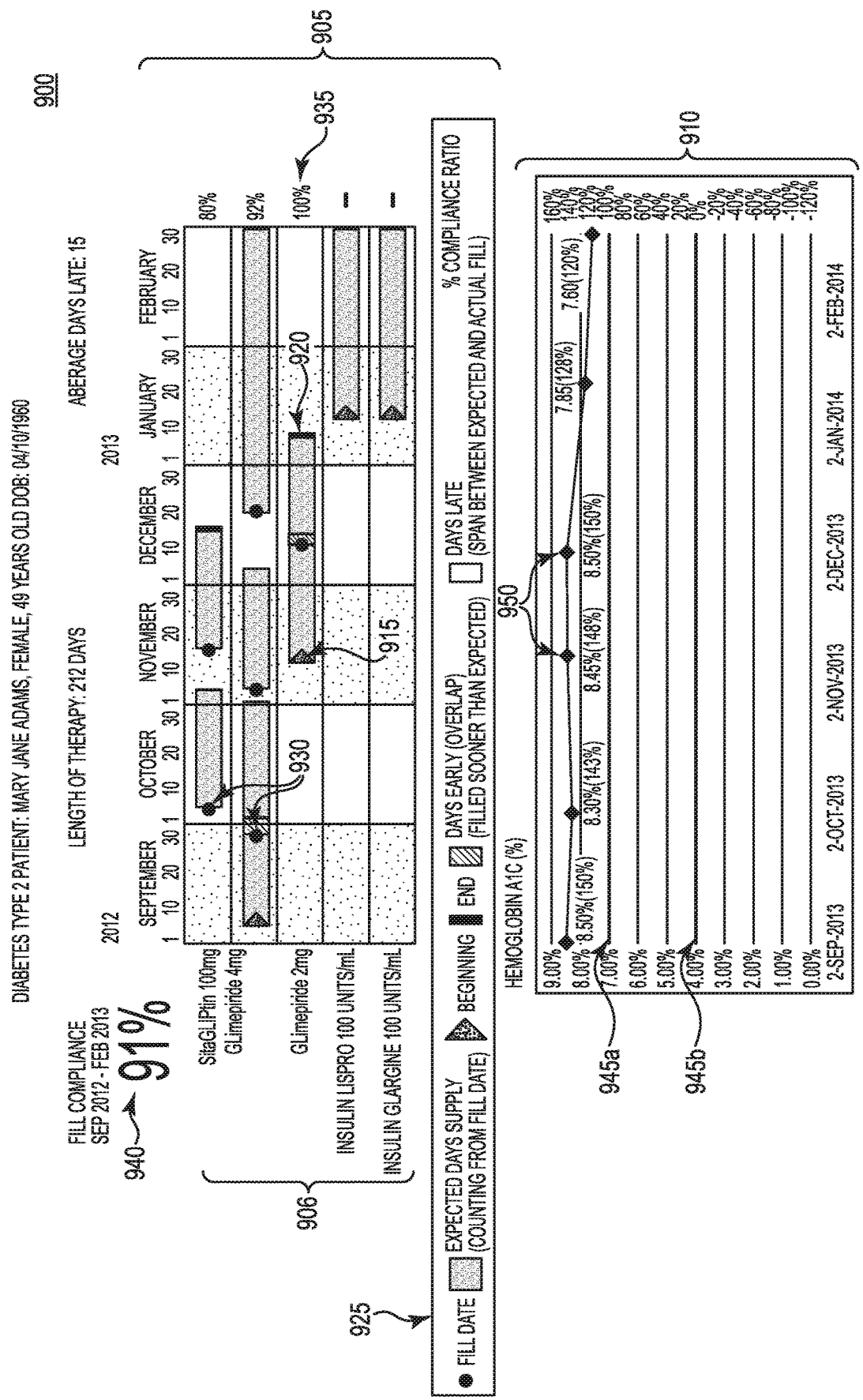
FIG. 7 is an example of a graphical presentation of prescription fill information and lab values according to an embodiment of the disclosure.

FIG. 7 is an example of a graphical presentation 900 of prescription fill information 905 and lab values 910 according to an embodiment of the disclosure. In this example, a patient is on five prescription medications 906. The adherence for each medication during a period of time may be shown on individual lines. Similar to FIG. 6, arrows 915 may be used to indicate when a prescription commenced and lines 920 may be used to indicate when the prescription ended and/or expired. Circles 930 may indicate when the patient filled a prescription. For example, glimepiride was begun in mid-November 2012, was filled in early December, and ended in early January 2013. In some embodiments, the graphical presentation 900 may include different colors and/or shadings of different time periods of the medications 906 that may reflect the patient's level of adherence during the time period for the medication. The graphical presentation 900 may further include a legend 925 to correspond the different colors and/or shadings to different adherence levels. Individual adherence scores 935 for each medication may be displayed, in addition to an overall adherence score 940.

As shown in FIG. 7, individual lab values 950 may be plotted over time. The normal and/or desired range may be indicated by upper and lower bounds 945a-b. In this example, the patient's hemoglobin A1C is measured to be consistently above the upper bound 945a of a desired range. The adherence data 905 and lab values 910 may be displayed so that their timelines are aligned. Although circles, arrows, and lines are used in the example shown in FIG. 7, other symbols may be used. For example, "X" may be used instead of diamonds 950 to indicate an individual lab result.

Figure 8:
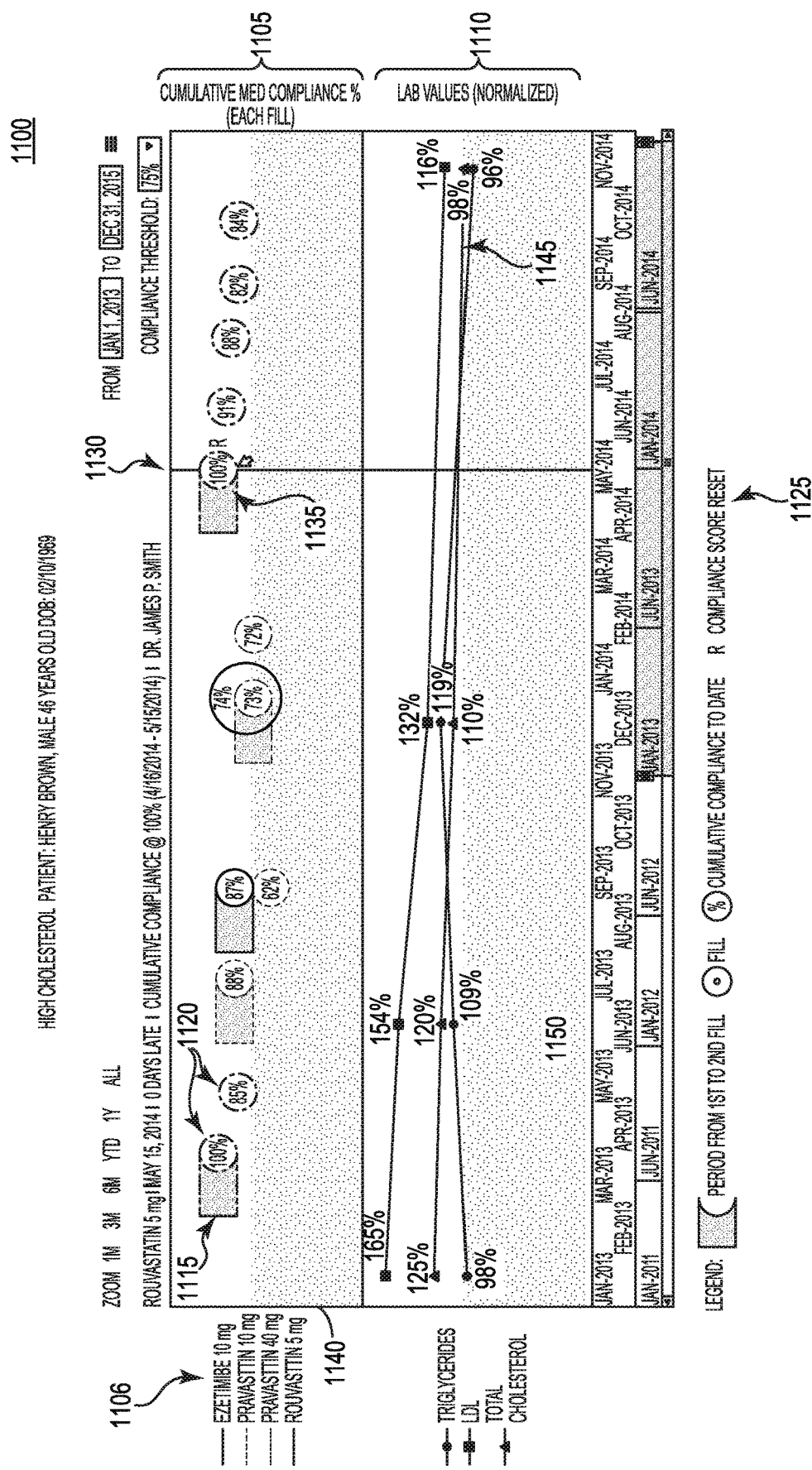
FIG. 8 is an example of a graphical presentation of prescription fill information and lab values according to an embodiment of the disclosure.

FIG. 8 is an example of a graphical presentation 1100 of prescription fill information 1105 and lab values 1110 according to an embodiment of the disclosure. In this example, a patient is on four prescription medications 1106. The adherence for each medication during a period of time may be shown on individual lines. Bars 1115 may be used to indicate when a prescription commenced and circles 1120 may be used to indicate when the prescription was refilled. Inside the circle 1120 may be the calculated adherence score. For example, rosuvastatin 5 mg was begun in mid-February 2013, was filled in March 2013 with an adherence score of 100%, and again in May 2013 with an adherence score of 85%. In some embodiments, the graphical presentation 1100 may display the bars 1115 and circles 1120 of different time periods of the medications 1106 at different heights that may reflect the patient's level of adherence during the time period for the medication. The graphical presentation 1100 may further include a shaded region and/or line 1140 that may indicate a threshold adherence score. The graphical presentation 1100 may further include a legend 1125 to correspond the different colors, icons and/or shadings to different adherence levels.

The graphical presentation 1100 may include a vertical bar 1130 that a user may drag to select a specific point in time. The graphical presentation 110 may include a feature that may allow a clinician to reset a patient's adherence score calculation. For example, as shown in FIG. 8, the rosuvastatin 5 mg is not refilled from June 2013 until April 2014. If this long period of no fills is due to the patient discontinuing the medication on the advice of the clinician (e.g., ended medication, changed dose of medication, and/or changed medication type), the lack of fills should be prevented from affecting the adherence score. In some embodiments, an adherence manager may solicit input to a patient to request whether or not the clinician chose to discontinue a medication. In some embodiments, the clinician may elect to reset the adherence calculation when a medication is discontinued and/or restarted. A reset point may be indicated by an "R" 1135 or other symbol. For example, when rosuvastatin 5 mg is restarted in April 2014, the adherence calculation is reset, allowing the adherence score to be calculated as 100% in May 2014. Without the reset, the adherence score would have been 21%. This low adherence score may have falsely ranked the patient as higher risk.

As shown in FIG. 8, individual normalized lab values 1150 may be plotted over time. The normal and/or desired range may be indicated by a shaded region 945. In this example, the patient's is triglycerides measured to be at the upper edge or above the upper bound of the normal range 1150. The adherence data 1105 and lab values 1110 may be displayed so that their timelines are aligned. Although circles, arrows, and lines are used in the example shown in FIG. 8, other symbols may be used. For example, "X" may be used instead of circles 1150 to indicate an individual lab result.

Figure 9:
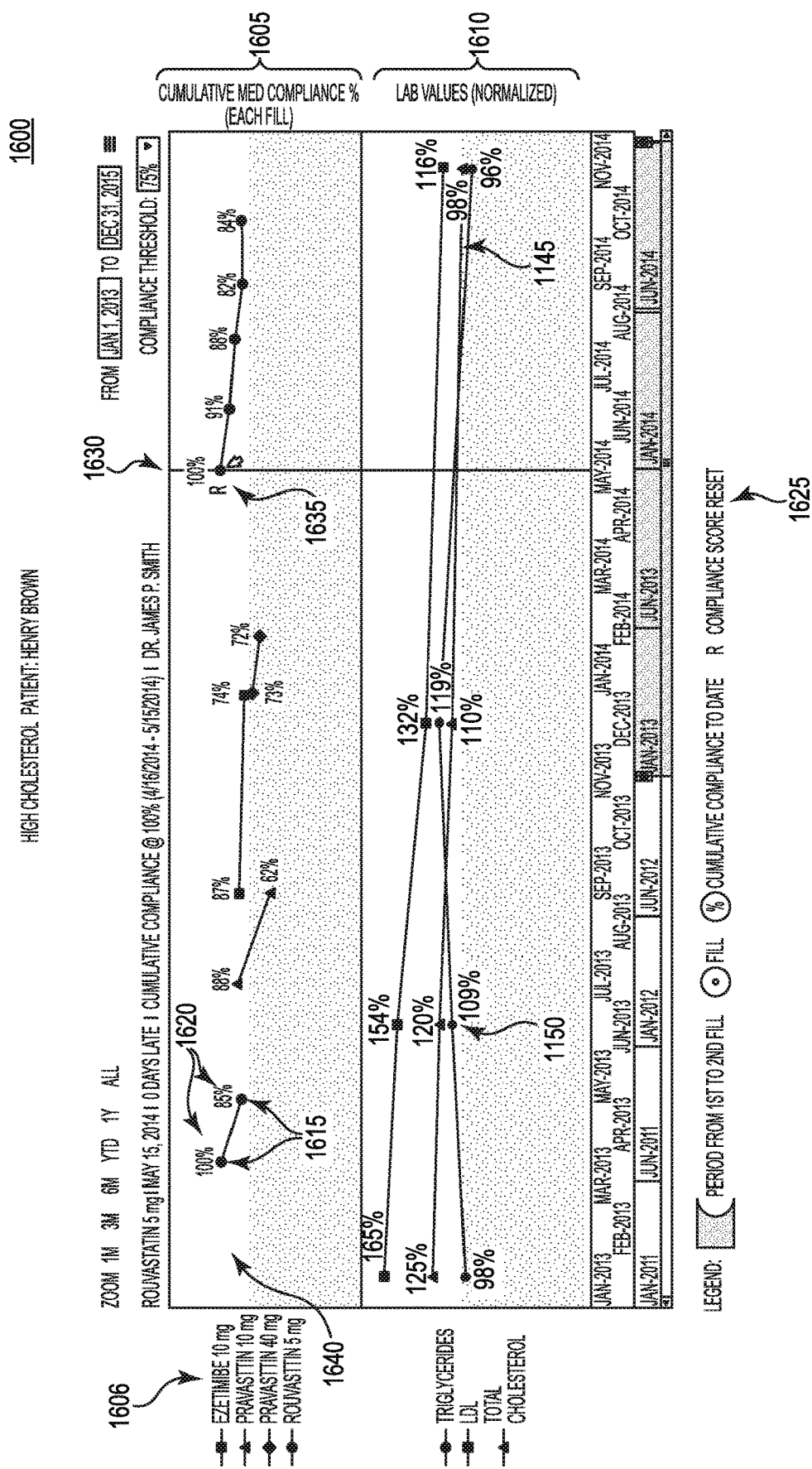
FIG. 9 is an example of a graphical presentation of prescription fill information and lab values according to an embodiment of the disclosure.

FIG. 9 is an example of a graphical presentation 1600 of prescription fill information 1605 and lab values 1610 according to an embodiment of the disclosure. In this example, a patient is on four prescription medications 1606. The adherence for each medication during a period of time may be shown by individual plots. Points 1615 may be used to indicate when a prescription commenced or was refilled, and may be connected by lines. The calculated adherence scores 1620 may be adjacent to each point 1615. For example, rosuvastatin 5 mg was begun in March 2013, was refilled in April 2013 with an adherence score of 85%. In some embodiments, the graphical presentation 1600 may display the points 1615 of different time periods of the medications 1606 at different heights that may reflect the patient's level of adherence during the time period for the medication. The graphical presentation 1600 may further include a shaded region and/or line 1640 that may indicate a threshold adherence score. The graphical presentation 1600 may further include a legend 1625 to correspond the different colors, icons and/or shadings to different adherence levels.

The graphical presentation 1600 may include a vertical bar 1630 that a user may drag to select a specific point in time. The graphical presentation 1600 may include a feature that may allow a clinician to reset a patient's adherence score calculation. For example, as shown in FIG. 9, the rosuvastatin 5 mg is not refilled from May 2013 until May 2014. If this long period of no fills is due to the patient discontinuing the medication on the advice of the clinician (e.g., ended medication, changed dose of medication, and/or changed medication type), the lack of fills should be prevented from affecting the adherence score. In some embodiments, an adherence manager may solicit input to a patient to request whether or not the clinician chose to discontinue a medication. In some embodiments, the clinician may elect to reset the adherence calculation when a medication is discontinued and/or restarted. A reset point may be indicated by an "R" 1635 or other symbol. For example, when rosuvastatin 5 mg is restarted in May 2014, the adherence calculation is reset, allowing the adherence score to be calculated as 100%. Without the reset, the adherence score would have been artificially low. This low adherence score may have falsely ranked the patient as higher risk.

Figure 10:
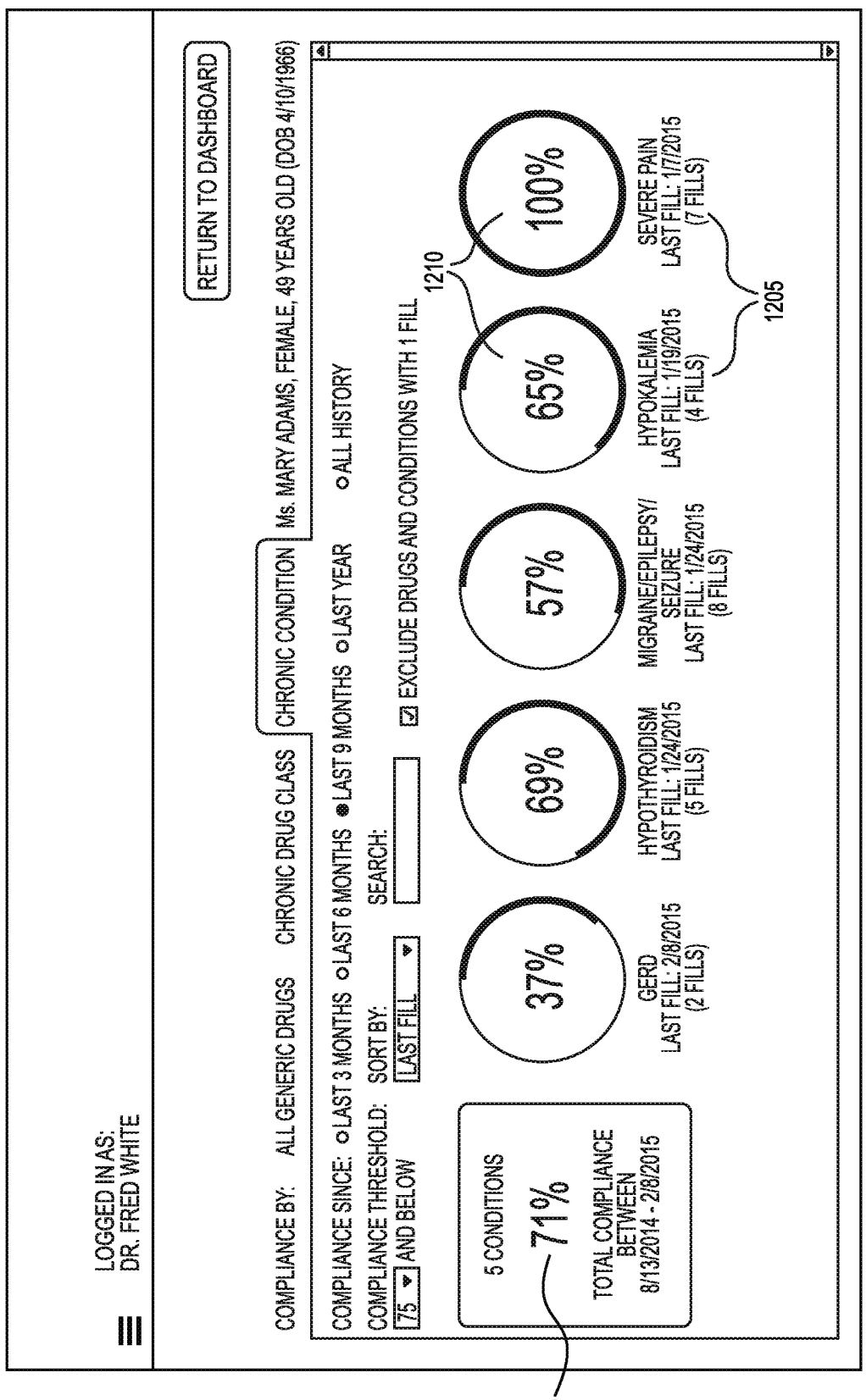
FIG. 10 is an example of a graphical presentation of prescription fill information and lab values according to an embodiment of the disclosure.

FIG. 10 an example of a graphical presentation 1200 of adherence to medications across conditions according to an embodiment of the disclosure. The adherence manager may allow medications to be linked to a condition or conditions for which the medications were prescribed to treat. The adherence manager may allow a clinician to view all conditions 1205 for which a patient is being treated. A composite adherence score 1210 may be provided for each condition. That is, the adherence score for each medication linked to a condition are combined into a single adherence score 1210. A combined adherence score 1125 across all conditions may also be provided.

Figure 11:
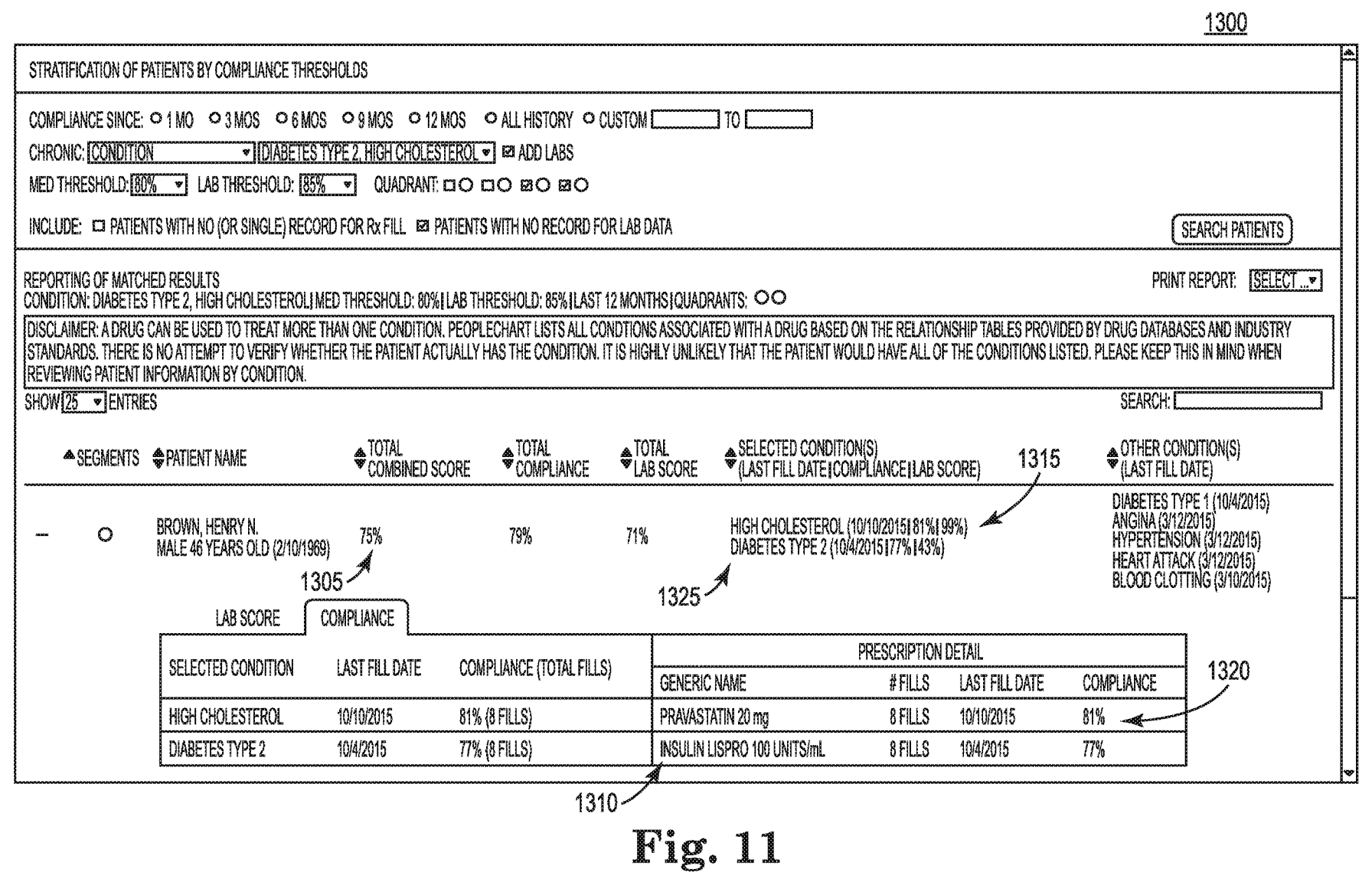

FIG. 11 is an example of a graphical presentation 1300 of an adherence score, lab value scores, and a combined score according to an embodiment of the disclosure. In this example, all of the lab scores 1315 are displayed for a particular condition 1325. The graphical presentation 1300 may provide an adherence score 1320. The adherence score 1320 may be calculated based on fill information for one or more medications linked 1310 to the particular condition 1325. The adherence score 1320 and lab score or scores 1315 may be used to calculate a combined score 1305. The combined score may be calculated using one of the equations described in reference to FIG. 4 or by another method.

Figure 12:
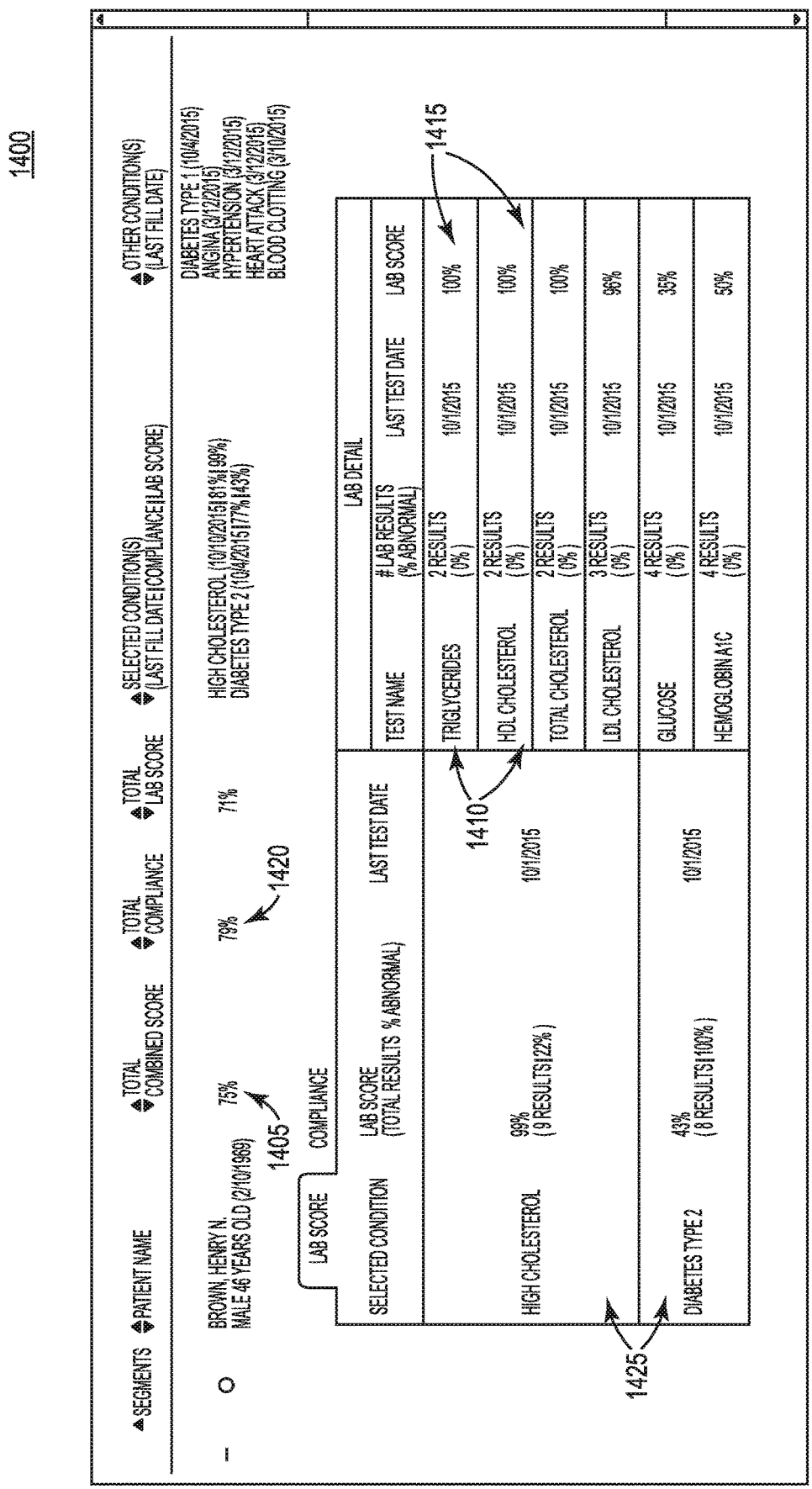
FIG. 12 is an example of a graphical presentation of prescription fill information, lab values, adherence score, and combined score according to an embodiment of the disclosure.

FIG. 12 is another example of a graphical presentation 1400 of an adherence score, lab value scores, and a combined score according to an embodiment of the disclosure. In this example, all of the lab scores 1415 are displayed for a particular condition 1425. The lab scores 1415 for more than one time point may be displayed. The lab scores 1415 for different tests 1410 may be displayed. The graphical presentation 1400 may provide an adherence score 1420. The adherence score 1420 may be calculated based on fill information for one or more medications linked to the particular condition 1325. The adherence score 1320 and lab score or scores 1315 may be used to calculate a combined score 1305. The combined score may be calculated using one of the equations described in reference to FIG. 4 or by another method.

Figure 13:
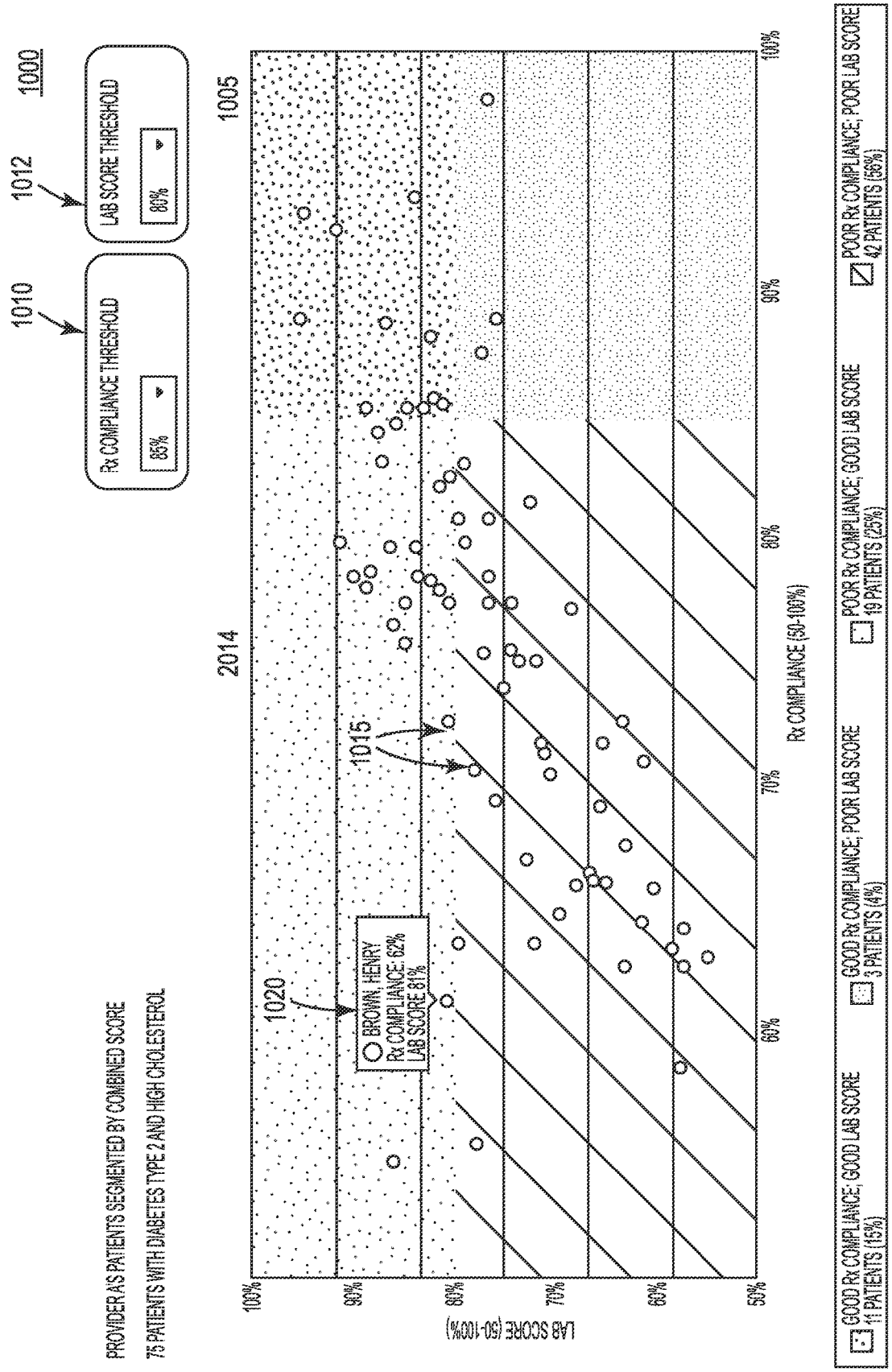
FIG. 13 is an example of a graphical presentation of prescription fill information and lab scores for a patient population according to an embodiment of the disclosure.

FIG. 13 is an example of a graphical presentation 1000 of prescription fill information and lab values for a patient population according to an embodiment of the disclosure. An adherence manager may allow a clinician to view data for populations of patients. The adherence manager may categorize, rank, and/or prioritize patients based, at least in part, on adherence and lab value scores. This may allow a clinician to determine which patients may be most in need of an intervention involving the clinician. In FIG. 13, a scatter plot 1005 includes four categories of patients. More or fewer categories may be defined. The categories may be labeled and/or color coded. In the example shown in FIG. 13, patients in the lower left quadrant have low adherence scores and lab value scores (e.g., non-adherent and abnormal lab values). The clinician and/or the adherence manager may flag these patients as high risk and prioritize them for individual follow up.

The clinician may view the entire patient population or a sub-set of the population. For example, as shown in FIG. 13, the clinician may choose to view only those patients being treated for high cholesterol and Type 2 Diabetes. The clinician may adjust the quadrants defining the four categories of patients by adjusting the adherence score threshold 1010 and lab score thresholds 1012. For example, the clinician may set a threshold value for the adherence score (or interchangeably compliance) 1010 for when the adherence manager determines an intervention may be required. More or fewer settings may be provided to the clinician for customization. Each data point 1015 represents a patient in the population. A clinician may select and/or hover over a data point 1015 to view more information 1020 about an individual patient. A clinician may select a data point 1015 to bring up full records for an individual patient. The records may be displayed in a graphical presentation such as the examples shown in FIGS. 6-12 or in another manner.

Figure 14:
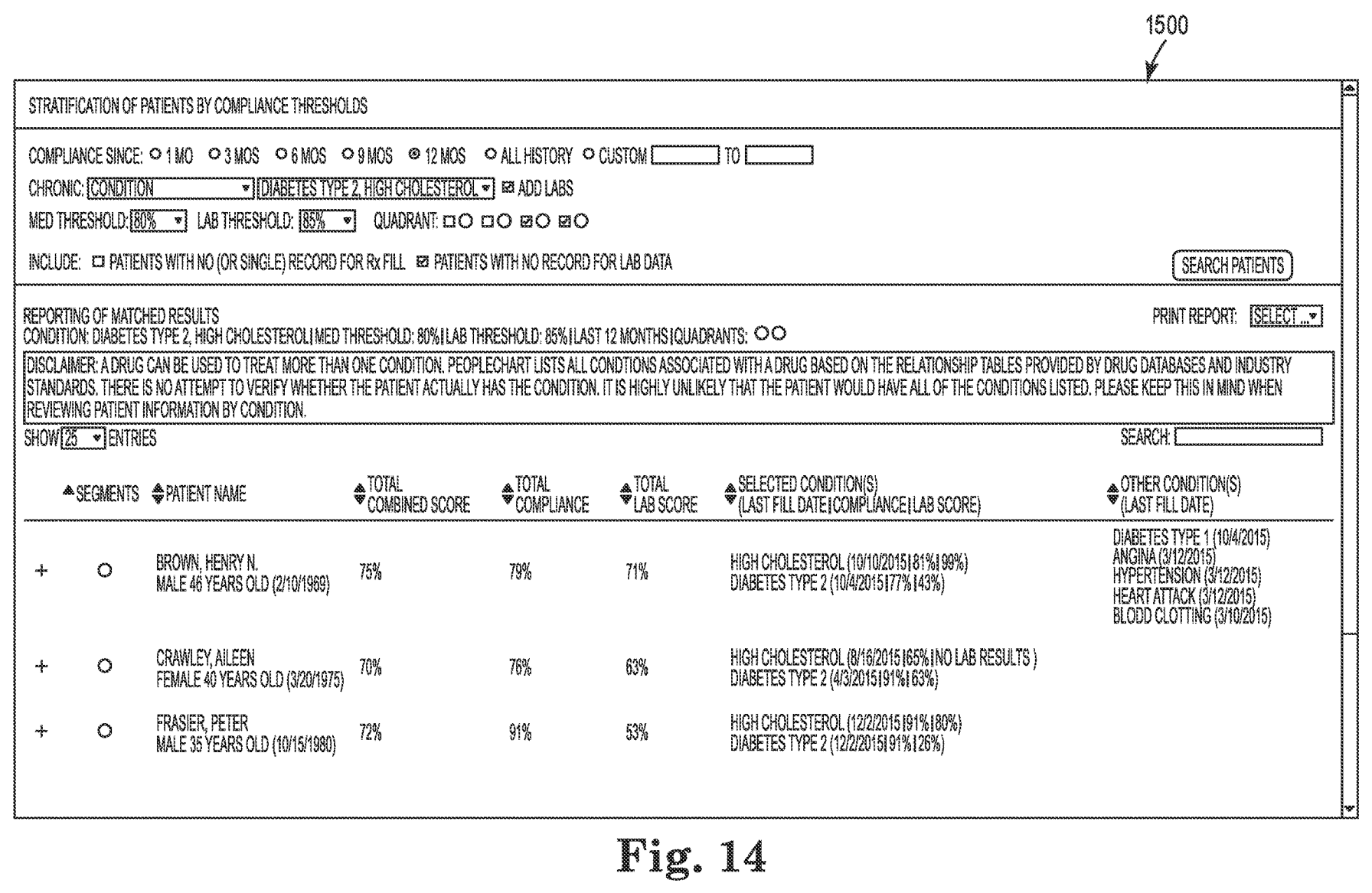

FIG. 14 is an example of a graphical presentation 1500 of a list of individual patients according to an embodiment of the disclosure. The clinician may view a list of individual patients by selecting a category, such as the categories displayed in the scatter plot 1005 shown in FIG. 13. In some embodiments, the list may depict same selected patients as represented in the scatter plot 1005. Other methods for viewing the list may be used. The list may include all patients in the clinician's practice or the list may be a subset of patients being treated for a particular condition and/or with a particular medication. The list of individual patients may be ranked based on adherence score, lab value score, combined score, and/or other criteria (e.g., age, last name, number of medications). In some embodiments, the list of patients displayed in graphical presentation 1500 may be generated from the scatter plot 1005. In some embodiments, the list of patients may be generated by the adherence manager by filtering patients based on search or categorization parameters (e.g., below an adherence threshold, lab score threshold, or with specific health condition(s)) as selected by the clinician. In some embodiments, the clinician may be able to select a patient from the list and be provided with a graphical presentation for the patient, such as graphical presentations shown in FIGS. 6-12.

Figures 15B, 15C:
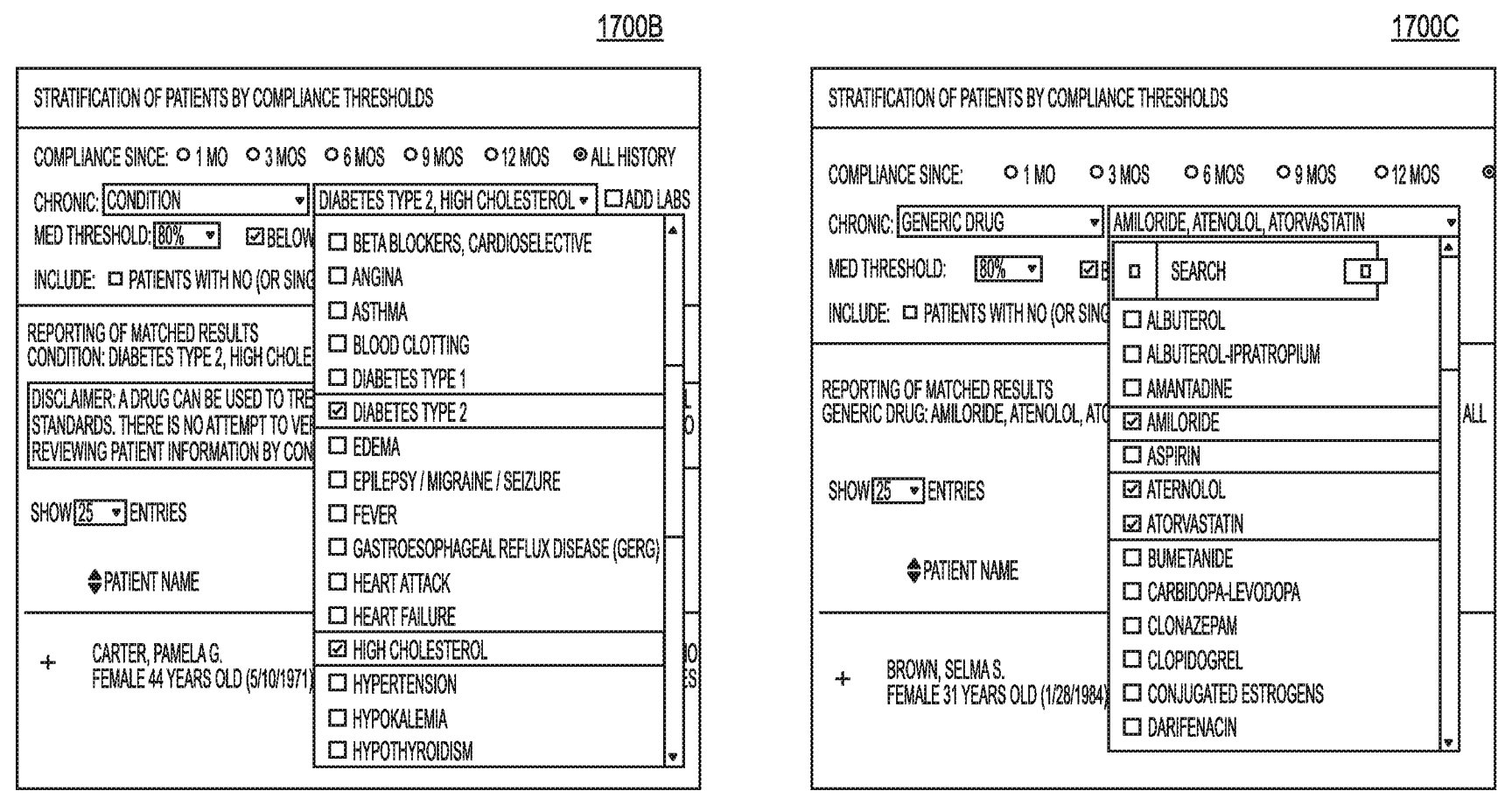

FIGS. 15*a-c* are examples of a graphical user interface 1700*a-c* according to an embodiment of the disclosure. The adherence manager may allow a clinician to search for patients based on a variety of factors. As shown in FIG. 15*a*, a clinician may search for patients prescribed one or more classes of drugs by making selections from a drop-down menu 1705. The clinician may select one or more drug classes. In the example shown in FIG. 15*a*, the clinician has selected beta blockers and HMG-CoA reductase inhibitors. In some embodiments, the adherence manager may allow a clinician to search for patients suffering from one or more conditions. In the example shown in FIG. 15*b*, the clinician has selected Type 2 Diabetes and high cholesterol. More or fewer conditions may be selected. In some embodiments, the adherence manager may allow a clinician to search for patients prescribed a particular drug or drugs. In the example shown in FIG. 15*c*, the clinician has selected aMLoride, atenolol, and atorvastatin. Based on the clinician's selections, the adherence manager may provide a sub-population of patients. The sub-population may be provided as a list, such as the list shown in FIG. 14. The sub-population may be provided as a scatter plot such as the plot shown in FIG. 13. Other methods of providing the sub-population may also be used.

The search selections shown in FIGS. 15a-c may be combined by the adherence manager into a single search in some embodiments. For example, a clinician may be able to search for patients with a certain condition taking a certain drug. Other combinations may also be used. This may allow a clinician to quickly determine patients that may be at high risk for complications. For example, a certain drug may be more likely to have adverse effects in patients suffering from a certain condition. A clinician may want to have higher adherence and lab value thresholds for those patients.

The graphical presentations illustrated in FIGS. 6-15 are exemplary and are not meant to be limiting to how the adherence scores, lab value scores, and/or combined scores may be displayed. In some embodiments, the graphical displays may be modified based on the device on which the data is displayed. For example, a clinician may be provided a different graphical presentation when viewing data on a mobile device than when viewing the data on a desktop computer. In some embodiments, the clinician may customize the graphical presentation to suit personal preferences and/or medical requirements. In some embodiments, the adherence manager may be operable without interaction with a display.

A non-limiting example is provided for better understanding of the embodiments described herein. The embodiments are not limited to the example provided herein.

A medication adherence system, such as the adherence manager describe in FIG. 2, may determine:

Is the patient adherent in filling prescribed medication or medications for the treatment of a condition whose outcome is also associated with a specific lab result or set of lab values?

If the system determines non-adherence, the system further determines: What can be done to improve patient adherence to the level required to achieve the previous, best-practice treatment regimen and what other medications or treatment regimens should be considered that may help the patient improve adherence (e.g., reduce bad side effects) while keeping in mind the need for treatment of the patient's primary condition?

If the system determines adherence, the system further determines: Is the prescribed treatment appropriate for this patient in terms of its desired impact on health outcomes (e.g., as reflected in the patient's lab values)? If not, should changes be considered in the prescribed treatment (e.g., changing the dosage)?

The medication adherence system may have reporting and stratification functions. The system may provide patients' medication adherence at the same time as lab values during physician review as part of a process for making new healthcare decisions. Diagnostic or biometric data combined with medication fill data may provide a limited and systematic set of hypotheses that may explain the reasons and/or causes of the patients' health outcomes based on stratification metrics.

An example of stratification metrics may include placing patients into one of four quadrants based on their individual "good" or "poor" lab values and/or "good" or "poor" adherence. Examples of the hypotheses drawn from these metrics that can prompt for the need to change treatment choices for the need to engage the patient in order to improve adherence are provided below. The combination of stratification metrics and hypotheses are summarized in FIG. 16.

The medication adherence system may be programmed to automatically take steps based at least in part on the combination and classification of the lab values and adherence behavior:

First Quadrant: Good Lab Values/Good Adherence (Low Risk Patients):

Goal: Monitor periodically. Little need for close and costly monitoring.

System to verify good adherence with patient.

If good adherence is false, system reassigns patient to segment "good lab values/poor adherence". (Follow steps applied to that group.)

If good adherence is true, system auto-messages patient to encourage adherence, remind need for periodic tests as part of status update, and ask "how feeling?"

Based on patient response on how feeling, system prompts clinician to consider reducing or discontinuing medication altogether.

Second Quadrant: Good Lab Values/Poor Adherence (Low-Moderate Risk Patients):

Goal: Find out reasons for improved outcomes.

System to verify poor adherence with patient. For example, ask patient if taking samples or stock-piled supply of prescribed medication.

If poor adherence is false, system reassigns patient to "good lab values/good adherence" group. (Follow steps applied to that group.)

If poor adherence is true, system auto-messages patient to evaluate any improvements in lifestyle and/or diet. If yes, move patient to "good adherence, good lab values".

If outcome improvement is driven by patient, system prompts clinician to consider reducing or discontinuing medication altogether.

If outcome improvement is not driven by patient, system prompts clinician to consider the possibility of (1) misdiagnosis or (2) effects from other conditions (co-morbidities).

Third Quadrant: Poor Lab Values/Good Adherence (Moderate-High Risk Patients):

Goal: Find out reasons for poor outcomes.

System to verify good adherence with patient. For example, ask patient if truly taking medication? Ask patient "how feeling?" (Gauge negative impact of side effects.)

If good adherence is false, system reassigns patient to "poor lab values/poor adherence" group. (Follow steps applied to that group.)

If good adherence is true, system prompts clinician to look into possible treatment-related reasons for poor outcome. For example, ask clinician to consider Prescribed treatment is inappropriate (not effective) for this patient or dosage prescribed may be insufficient;

Treatment may have counteractions with another drug that reduces the effectiveness of the current drug;

Patient's condition may have been misdiagnosed. Order same or different set of tests to provide more information about presence of other condition(s).

Fourth Quadrant: Poor Lab Values/Poor Adherence {High Risk Patients}.

Goal: Work on improving adherence first.

System to verify poor adherence with patient. For example, ask patient if taking samples or stock-piled supply of prescribed medication.

If poor adherence is false, system reassigns patient to "poor lab values/good adherence" group. (Follow steps applied to that group.)

If poor adherence is true, system prompts clinician for direct intervention, i.e., reach out to patient to ask how feeling (e.g., gauge side effects) and to solicit possible reasons for poor adherence (e.g., cost of drugs is prohibitive, side effects of drugs leads patient to avoid taking it as directed, patient simply forgets to take drug, patient is taking many different drugs which make schedule keeping difficult).

System reminds clinician that there is insufficient information to evaluate appropriateness of prescribed treatment. Premature to change medication unless for mitigating side effects. Poor adherence may be key factor contributing to patient's poor lab values/outcomes.

The placement of the patient into a specific quadrant may help lead to systematic treatment processes that can be executed through an automated messaging system and/or through human-assisted intervention. The medication adherence system may assist physicians to first determine whether the issue of patient adherence might explain poor outcomes as reflected in lab values. Linking adherence and lab values to the same condition may occur even in situations when patients are taking multiple medications and have multiple conditions. This may facilitate the ability to gauge the impact of medications on health outcome.

Threshold levels and criteria used to allocate patients to different quadrants, and the decision rules for patients in different groups, such as quadrants described in the example provided above, may vary, based on a patient's conditions, patient population being treated, guidelines for treatment that are specific to an individual healthcare provider, and/or level of overall resources and time available to allocate to the care of patients with various conditions, characteristics, and risk levels.

In complex situations in which the patient is being treated for multiple conditions and taking multiple prescriptions (treatment regimens), the medication adherence system may offer physicians a systematic and focused approach that may limit the scope of information to that which is relevant for decision-making, condition by condition.

The adherence management system may provide more complete data faster by combining lab results and prescription fill information that are typically provided separately. From the hypotheses and algorithms for scoring, physicians may select their treatment options about whether to change prescriptions based on a review of lab values for each condition in combination with medication adherence information. Hence, the systematic combination of lab values with relevant medication adherence data may allow providers and patients to focus on treatment options that may be more often consistent with best practice behaviors (both patient's and physician's) and best practice treatments. The result may be better alignment with best practice treatments and overall improvements in health outcomes.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the above is a complete description of selected embodiments of the present disclosure, it is possible to practice the invention use various alternatives, modifications, combinations and equivalents. In general, in the following claims, the terms used in the written description should not be construed to limit the claims to specific embodiments described herein for illustration, but should be construed to include all possible embodiments, both specific and generic, along with the full scope of equivalents to which such claims are entitled. Accordingly, the invention is not limited by the disclosure except by the following claims.

What is claimed is:

1. A method comprising:
    receiving, via one or more input devices, prescription information for a patient, wherein the prescription information comprises data indicative of a date when one or more prescriptions of the patient were ordered or picked up, name of the medication in the one or more prescriptions, name of a prescriber of the medication, number of days of supply in the one or more prescriptions of the patient, or a combination thereof;
    receiving, via the one or more input devices, lab values for the patient, wherein the lab values comprise a diagnostic result, a biometric result, or a combination thereof, for at least two different points in time;
    calculating, by a processor in communication with the one or more input devices, an adherence score based, at least in part, on the prescription information, wherein the calculating the adherence score includes determining an adherence percentage for a time interval that includes the at least two different points in time;
    calculating, by the processor, a lab score based, at least in part, on the lab values, wherein the calculating the lab score includes normalizing the lab values for the patient;
    analyzing, by the processor, the adherence score and the lab score to determine an intervention based at least in part, on the adherence score and the lab score, wherein the analyzing comprises comparing the adherence score to an adherence threshold value stored in a memory device in communication with the processor and comparing the lab score to a lab score threshold value stored in the memory device;
    generating, by the processor, a first type of alert and initiating a transmission of the first type of alert to the patient, a clinician providing health care to the patient, or both, if the lab score is below the lab score threshold value and the adherence score is above the adherence threshold value;
    generating, by the processor, a second type of alert and initiating a transmission of the second type of alert to the patient, the clinician, or both, if the lab score is above the lab score threshold value and the adherence score is below the adherence threshold value; and
    generating, by the processor, a third type of alert and initiating a transmission of the third type of alert to the patient, the clinician, or both, if the lab score is below the lab score threshold value and the adherence score is below the adherence threshold value.

2. The method of claim 1, further comprising generating, by the processor, an automated message prompting the patient to take action to improve adherence if the adherence score is below the adherence score threshold value.

3. The method of claim 2, further comprising generating, by the processor, an alert to the clinician prompting the clinician to take action responsive to a particular patient response or non-response to the automated message.

4. The method of claim 1, wherein calculating the adherence score comprises dividing an expected days-supply by a number of days elapsed between fills.

5. The method of claim 1, further comprising:
soliciting a response from the patient; and
receiving a response from the patient.

6. The method of claim 5, further comprising calculating a patient response score based on the response from the patient.

7. The method of claim 6, wherein the patient response score and a single score formed from a combination of the adherence score and the lab score are evaluated to determine an intervention.

8. The method of claim 1, wherein the adherence score and the lab score are combined to form a single score to determine an intervention.

9. The method of claim 1, wherein the method further comprises weighting the adherence score or lab score prior to comparing the adherence score to the adherence score threshold value or the lab score to the lab score threshold value.

10. The method of claim 9, wherein the adherence score threshold value is different from the lab score threshold value.

11. The method of claim 7, wherein the single score is generated by further combining the adherence and lab scores with a patient response score that is based on a response of the patient to the message prompting the patient for information.

12. An adherence manager comprising:
a memory accessible to one or more processors, the memory having patient lab values and prescription information stored thereon, wherein the prescription information comprises data indicative of a date when one or more prescriptions of the patient were ordered or picked up, name of the medication in the prescription, name of the prescriber of the medication, number of days of supply in the one or more prescriptions of the patient, or a combination thereof, and wherein the patient lab values comprise a diagnostic result, biometric result, or a combination thereof, for at least two different points in time;
a first database accessible to the one or more processors, the first database having diagnostic tests and conditions associated with the diagnostic tests stored therein;
a second database accessible to the one or more processors, the second database having prescriptions and conditions associated with the prescriptions;
a mapping processor configured to access the memory, the mapping processor further configured to map the patient lab values to the patient prescription information corresponding to the patient lab values and output a selection of the patient lab values and corresponding selected patient prescription information;
a score processor, in communication with the mapping processor and the first and second databases, the score processor being configured to calculate an adherence score and a lab score, based, at least in part, on the selection of patient lab values and patient prescription information received from the mapping processor, wherein the adherence score is calculated by determining an adherence percentage for a time interval that includes the at least two different points in time, wherein the processor is configured to normalize the selection of patient lab values for calculating the lab score, and wherein the score processor is further configured to compare the adherence score to an adherence score threshold value and compare the lab score to a lab score threshold value to determine an intervention,
wherein the intervention includes generating a first type of alert and transmitting, responsive to the first type of alert, a message to a clinician providing healthcare to the patient if the lab score is below the lab score threshold value and the adherence score is above the adherence score threshold value;
wherein the intervention includes generating a second type of alert and transmitting, responsive to the second type of alert, a message to the patient if the lab score is above the lab score threshold value and the adherence score is below the adherence score threshold value; and
wherein the intervention includes generating a third type of alert and transmitting, responsive to the third type of alert, a message to both the patient and the clinician if the lab score is below the first lab score threshold value and the adherence score is below the adherence score threshold value.

13. The adherence manager of claim 12, further comprising an alerting system configured to send an automated message to at least one of a patient device or a clinician device responsive to the score processor.

14. The adherence manager of claim 13, wherein the alerting system is further configured to receive a response from the patient device and provide the response to the clinician device.

15. The adherence manager of claim 13, wherein the alerting system is further configured to send an automated message to the patient device based on a signal received from the clinician device.

16. The adherence manager of claim 13, wherein the automated message is at least one of a text message, an e-mail, a telephone call, or other notification.

17. The adherence manager of claim 12, wherein the score processor is further configured to provide the lab score and the adherence score to a clinician device.

18. The adherence manager of claim 12, wherein the score processor is further configured to calculate a plurality of lab scores and adherence scores corresponding to a plurality of patients, combine the plurality of lab scores and adherence scores into a plurality of combined scores, and provide the plurality of combined scores to a clinician device.

19. The adherence manager of claim 18, wherein the score processor is further configured to numerically rank the plurality of combined scores.

20. The adherence manager of claim 18, wherein the clinician device includes a display and a graphical user interface configured to provide the plurality of combined scores in graphical form on the display.

21. The adherence manager of claim 12, wherein the patient prescription information is provided by a pharmacy.

22. The adherence manager of claim 12, wherein the patient lab values are provided by a laboratory center.

23. The adherence manager of claim 12, wherein the mapping processor and the score processor are integrated into a single processor.

24. A method comprising:
receiving, via one or more input devices, prescription information for a patient, wherein the prescription information comprises data indicative of a date when one or more prescriptions of the patient were ordered or picked up, name of the medication in the one or more prescriptions, or a combination thereof;
receiving, via the one or more input devices, a plurality of lab values for the patient, wherein at least one of the plurality of lab values is associated with at least one respective condition for which the patient has been prescribed the medication in the one or more prescriptions of the patient;

calculating, by a processor in communication with the one or more input devices, an adherence score and a lab score, wherein the adherence score is based, at least in part, on the prescription information, and wherein the lab score is based, at least in part, on the at least one lab value associated with the at least one respective condition;

comparing, by the processor, the adherence score to an adherence score threshold value and the lab score to a lab core threshold value to determine an intervention based at least in part, on the comparison of the adherence score and the lab score to the respective one of the adherence score and lab score threshold values or on a single score generated by combining the adherence score and the lab score;

wherein the intervention incudes generating, by the processor, and transmitting an automated message prompting the patient for information if the adherence score is below the adherence score threshold value;

wherein the intervention includes generating, by the processor, and transmitting an automated message to a clinician treating the patient if the lab score is below the lab score threshold; and wherein the intervention includes generating, by the processor, and transmitting a respective automated message for the patient and the clinician if the lab score is below the lab score threshold value and the adherence score is below the adherence score threshold value.

25. The method of claim 24, wherein the interventions includes sending, by a notification system to an alerting system including at least one of a desktop computer, a hospital mainframe, a tablet computer, or a mobile phone, based on one or more of the calculated adherence and lab scores, an automated alert signal including at least one of a text message, an e-mail, an automated phone call, or a flag in the alerting system, and wherein the alert signal includes a patient record with the one or more of the calculated adherence and lab scores.

26. The method of claim 24, wherein the receiving prescription information further includes receiving, via the one or more input devices including at least one of a desktop computer, a tablet computer, and a mobile phone, a message including at least one of a text message, an e-mail, or an automated phone call, the message including prescription fill information for the patient, wherein the receiving lab values further includes receiving, via the one or more input devices, lab values for the patient, and storing, by a memory in communication with the processor, the received prescription information and the received lab values, wherein the calculating an adherence score further includes calculating, by the processor, the adherence score based, at least in part, on the prescription information, and wherein the calculating a lab score further includes calculating, by the processor, the lab score based, at least in part, on the lab values.

* * * * *